United States Patent
Kusumi et al.

(10) Patent No.: US 9,676,719 B2
(45) Date of Patent: Jun. 13, 2017

(54) PHENYL DERIVATIVE

(71) Applicant: ONO PHARMACEUTICAL CO., LTD., Osaka (JP)

(72) Inventors: Kensuke Kusumi, Osaka (JP); Atsushi Naganawa, Osaka (JP); Kazuhiro Otsuki, Osaka (JP); Tetsuya Sekiguchi, Osaka (JP); Koji Shinozaki, Osaka (JP); Hiroshi Yamamoto, Osaka (JP); Yasuko Yamamoto, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/780,152

(22) PCT Filed: Mar. 25, 2014

(86) PCT No.: PCT/JP2014/058211
§ 371 (c)(1),
(2) Date: Sep. 25, 2015

(87) PCT Pub. No.: WO2014/157158
PCT Pub. Date: Oct. 2, 2014

(65) Prior Publication Data
US 2016/0039757 A1  Feb. 11, 2016

(30) Foreign Application Priority Data

Mar. 26, 2013 (JP) ................. 2013-063304

(51) Int. Cl.
*C07D 211/52* (2006.01)
*C07D 207/12* (2006.01)
*C07D 211/44* (2006.01)
*C07D 211/48* (2006.01)

(52) U.S. Cl.
CPC .......... *C07D 211/52* (2013.01); *C07D 207/12* (2013.01); *C07D 211/44* (2013.01); *C07D 211/48* (2013.01)

(58) Field of Classification Search
CPC .. C07D 211/48; C07D 207/12; C07D 211/52; C07D 211/44
USPC ....................................................... 546/184
See application file for complete search history.

(56) References Cited

U.S. PATENT DOCUMENTS

| | | | |
|---|---|---|---|
| 8,975,409 B2 | 3/2015 | Naganawa et al. | |
| 2006/0148844 A1 | 7/2006 | Nakade et al. | |
| 2007/0135402 A1 | 6/2007 | Habashita et al. | |
| 2007/0167425 A1* | 7/2007 | Nakade ................ | C07C 229/14 514/210.17 |
| 2010/0121052 A1 | 5/2010 | Jain et al. | |
| 2010/0216767 A1 | 8/2010 | Aikawa et al. | |
| 2011/0269244 A1 | 11/2011 | Petter et al. | |
| 2012/0136002 A1 | 5/2012 | Goswami et al. | |
| 2014/0235611 A1 | 8/2014 | Naganawa et al. | |

FOREIGN PATENT DOCUMENTS

| | | |
|---|---|---|
| CN | 1590378 A | 3/2005 |
| EP | 0643076 A1 | 3/1995 |
| JP | 6 234797 A | 8/1994 |
| JP | 2009534440 A | 9/2009 |
| JP | 2010514693 A | 5/2010 |
| JP | 2011524881 A | 9/2011 |
| RU | 2390519 C2 | 5/2010 |
| WO | 0198301 A1 | 12/2001 |
| WO | 2004002531 A1 | 1/2004 |
| WO | 2005/020882 A2 | 3/2005 |

(Continued)

OTHER PUBLICATIONS

Adada; FEBS Journal 2013, 280, 6354-6366.*
Proia; J Clin Invest. 2015,125, 1379-1387.*
Office Action issued on Jan. 27, 2016, by the National Office of Intellectual Property in related Vietnamese Application No. 1-2014-01021.
Office Action issued on Feb. 1, 2016, by the Intellectual Property Office of Singapore in related Singaporean Application No. 11201400954R.
European Patent Office, Communication issued Oct. 21, 2016, in counterpart European Patent Application No. 14775353.7.
Search Report dated Oct. 23, 2012, issued by the International Searching Authority in International Application No. PCT/JP2012/074968.
Search Report dated Apr. 20, 2015, issued by the European Patent Office in counterpart European Application No. 12837524.3.
Search Report dated May 20, 2014, issued by the International Searching Authority in counterpart International Application No. PCT/JP2014/058211.

(Continued)

*Primary Examiner* — Noble Jarrell
*Assistant Examiner* — Daniel Carcanague
(74) *Attorney, Agent, or Firm* — Sughrue Mion, PLLC

(57) ABSTRACT

An object of the present invention is to provide a compound having strong human $S1P_2$ antagonistic activity in order to develop a useful medicament for therapy of a $S1P_2$-mediated disease such as a disease resulting from vascular constriction, fibrosis and respiratory disease. The compound represented by the general formula (I), wherein all the symbols have the same meanings as described in the specification, has a halogen atom or a haloalkyl group and a phenoxy group at certain substitution sites, and thus has strong human $S1P_2$ antagonistic activity. Therefore, the compound can be a therapeutic agent for a $S1P_2$-mediated disease, such as a disease resulting from vascular constriction, fibrosis and respiratory disease.

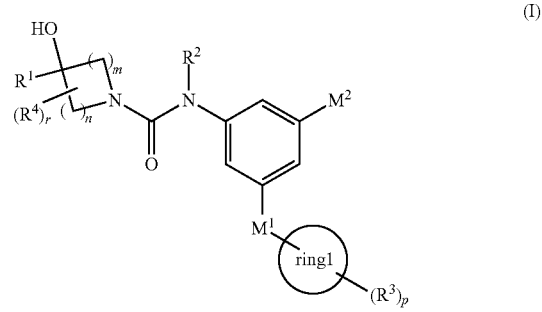

14 Claims, No Drawings

(56) References Cited

FOREIGN PATENT DOCUMENTS

| WO | 2005063704 A1 | 7/2005 |
| WO | 2007125049 A1 | 11/2007 |
| WO | 2010133748 A1 | 11/2010 |
| WO | 2011082285 A1 | 7/2011 |
| WO | 2011087051 A1 | 7/2011 |
| WO | 2013047701 A1 | 4/2013 |

OTHER PUBLICATIONS

Bonnie W. Ramsey; "Management of Pulmonary Disease in Patients with Cystic Fibrosis", Drug Therapy, The New England Journal of Medicine, Jul. 18, 1996, vol. 335, No. 3, p. 179-188.

Bromidge et al.; "Biarylcarbamoylindolines Are Novel and Selective 5-HT2C Receptor Inverse Agonists: Identification of 5-Methyl-1-[[2-[(2-methyl-3-pyridyl)oxy]-5-pyridyl]carbamoyl]-6-trifluoromethylindoline (SB-243213) as a Potential Antidepressant/Anxiolytic Agent", Journal of Medicinal Chemistry, 2000, vol. 43, No. 6, p. 1123-1134.

Venkatesh et al.; "Role of the Development Scientist in Compound Lead Selection and Optimization", Journal of Pharmaceutical Sciences, vol. 89, No. 2, Feb. 2000, p. 145-154.

John Wiley & Sons. Inc.; Burgers Medicinal Chemistry and Drug Discovery, Fifth Edition, vol. 1, Principles and Practice, p. 975-977, 1995.

West, Anthony R.; "Solid State Chemistry and its Application", 1984, p. 358 & 365.

Bolli et al.; "Synthetic Sphingosine 1-Phosphate Receptor Modulators—Opportunities and Potential Pitfalls", Current Topics in Medicinal Chemistry, 2011, vol. 11, No. 8, p. 726-757, XP 56110362A.

Freshney, R., "Culture of Animal Cells, A Manual of Basic Technique", Alan R. Liss, Inc., 1983, 3 pages total, New York, New York.

Roviezzo, et al., "Sphingosine-1-Phosphate Modulates Vascular Permeability and Cell Recruitment in Acute Inflammation In Vivo", The Journal of Pharmacology and Experimental Therapeutics, Vo. 337, Issue No. 3, 2011, pp. 830-837.

Kusumi, et al., "Discovery of novel $S1P_2$ antagonists. Part 2: Improving the profile of a series of 1,3-bis(aryloxy)benzene derivatives", Bioorganic & Medicinal Chemistry Letters 25, 2015, pp. 4387-4392.

United States Patent and Trademark Office, Communication issued Jan. 19, 2017, in co-pending U.S. Appl. No. 15/089,690.

Russian Patent Office, Communication dated Jan. 24, 2017, issued in corresponding Russian Application No. 2014117170/04.

State Intellectual Property Office of the People's Republic of China, communication dated Mar. 30, 2017, issued in corresponding Chinese Application No. 201480017929.3.

* cited by examiner

PHENYL DERIVATIVE

TECHNICAL FIELD

The present invention relates to a compound represented by the general formula (I):

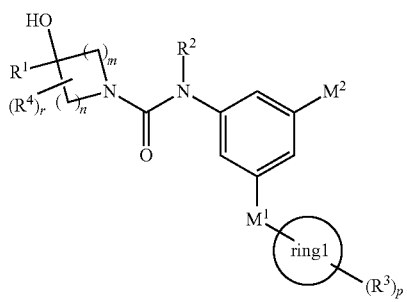

wherein all the symbols have the same meanings as described hereinbelow, and a salt thereof, a solvate thereof, an N-oxide thereof or a prodrug thereof (hereinafter sometimes abbreviated as the present compound).

BACKGROUND ART

Sphingosine-1-phosphate [(2S,3R,4E)-2-amino-3-hydroxyoctadeca-4-enyl-1-phosphate; hereinafter sometimes abbreviated as S1P] is a lipid which is synthesized by metabolic turnover of sphingolipids or extracellular action of secretory sphingosine kinases. It is proposed that this lipid acts as an intercellular transmitter and an intracellular secondary transmitter.

With regard to $S1P_2$ (EDG-5/AGR16/H218) receptors among S1P receptors, it has been published that the strong expression of mRNA thereof is confirmed in tissues of heart, lung, stomach and small intestine and that the expression amount of mRNA thereof in normal intimal cells in model mice of carotid balloon injury which are the model for coronary arteriosclerosis is significantly decreased compared to normal intimal cells (see Patent Document 1).

It is also reported that S1P receptors (particularly $S1P_2$ receptors) are involved in portal hypertension, asthma and the like (see Non Patent Document 1). It is also known that the receptors are involved in expression of connective tissue growth factors (CTGFs) associated with onset of fibrosis, cancer and the like (see Non Patent Document 2).

The following compounds are known as the related art of the present invention.

As the compounds having $S1P_2$ antagonistic activity, pyrazopyridine compounds or pharmaceutically acceptable salts thereof represented by the general formula (a):

[C 2]

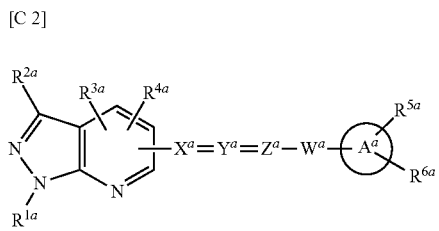

wherein $R^{1a}$, $R^{2a}$ and $R^{3a}$ represent a C1-8 alkyl group and the like; $R^{4a}$ represents a hydrogen atom and the like; $R^{5a}$ and $R^{6a}$ are the same or different and represent a hydrogen atom, a C1-8 alkyl group, a C1-6 alkoxy group, a halogen atom and the like; $X^a$ represents —NH—, —O—, —CH$_2$— and the like; $Y^a$ represents —NH— and the like; $Z^a$ represents —CO— and the like; $W^a$ represents —NH— and the like; and the ring $A^a$ represents an aryl group, a heteroaryl group and the like (the definitions of respective groups are abstracted), have been disclosed which specifically act on $S1P_2$ receptors and are useful as therapeutics for fibrosis (see Patent Document 2).

The known compounds having $S1P_2$ antagonistic activity also include compounds having a piperidine skeleton represented by the general formula (b):

[C 3]

$$A^b\text{-}X^b\text{-}Y^b\text{-}Z^b\text{-}B^b \quad (b)$$

wherein $A^b$ represents a cyclic group which may contain a substituent; $X^b$ represents a single bond or a spacer having 1 to 3 atoms in the backbone; $Y^b$ represents a single bond or a spacer having 1 to 3 atoms in the backbone; $Z^b$ is a single bond or a spacer having 1 to 3 atoms in the backbone; and $B^b$ represents a cyclic group which may contain a substituent (see Patent Document 3) and compounds having an azetidine skeleton (see Patent Document 4).

No prior art documents disclose or suggest that the compound of the invention which contains two specific substituents, particularly a halogen atom or a haloalkyl group and a phenoxy group at certain substitution positions can significantly improve human $S1P_2$ antagonistic activity.

Patent Document 1: Japanese Patent Application Laid-open No. H6-234797

Patent Document 2: WO 01/98301

Patent Document 3: WO 2004/002531

Patent Document 4: WO 2005/063704

Non Patent Document 1: Biochemical and Biophysical Research Communications, vol. 320, No. 3, p. 754-759, 2004

Non Patent Document 2: Molecular Cancer Research, vol. 6, No. 10, p. 1649-1656, 2008

DISCLOSURE OF THE INVENTION

An object of the present invention is to find a compound having human $S1P_2$ antagonistic activity which was insufficiently exhibited by the compounds disclosed in Patent Document 3, to improve the solubility of the compound and to provide a medicinal product thereof.

The present inventors have carried out extensive studies in order to solve the above problem and find the compound having improved human $S1P_2$ antagonistic activity. As a result, the present inventors have surprisingly found that the compound having specific substituents, particularly a halogen atom or a haloalkyl group and a phenoxy group at certain substitution positions has significantly improved human $S1P_2$ antagonistic activity compared to the compound disclosed in Patent Document 3, thereby completing the present invention.

Thus the present invention relates to:

[1] a compound represented by the general formula (I):

[C 4]

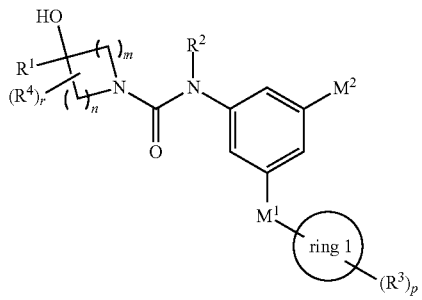

(I)

wherein $R^1$ represents (1) a C1-8 alkyl group which may be substituted with 1 to 5 $R^{21}$ groups, (2) a C2-8 alkenyl group which may be substituted with 1 to 5 $R^{21}$ groups, (3) a C2-8 alkynyl group which may be substituted with 1 to 5 $R^{21}$ groups or (4) a C3-7 carbocycle which may be substituted with 1 to 5 substituents selected from the group consisting of a C1-4 alkyl group, a C1-4 haloalkyl group, a C1-4 alkoxy group and a halogen atom;

$R^{21}$ represents (1) a halogen atom, (2) $OR^{22}$ (in the group, $R^{22}$ represents (1) a hydrogen atom, (2) a C1-4 alkyl group or (3) a C1-4 haloalkyl group), (3) —$NR^{23}R^{24}$ (in the group, $R^{23}$ and $R^{24}$ respectively and independently represent (1) a hydrogen atom or (2) a C1-4 alkyl group) or (4) an oxo group;

$R^2$ represents (1) a hydrogen atom, (2) a C1-4 alkyl group or (3) a C1-4 haloalkyl group;

$R^3$ represents (1) a halogen atom, (2) a C1-4 alkyl group, (3) a C1-4 haloalkyl group, (4) a C1-4 alkoxy group, (5) a hydroxy group, (6) -L-$CONR^6R^7$, (7) -L-$SO_2R^8$ or (8) -L-$COOR^9$;

$R^4$ represents (1) a halogen atom, (2) a C1-4 alkyl group or (3) a C1-4 haloalkyl group;

L represents (1) a bond, (2) a group represented by the formula:

[C 5]

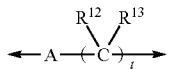

wherein A represents (1) a bond or (2) an oxygen atom; $R^{12}$ and $R^{13}$ respectively and independently represent (1) a hydrogen atom, (2) a C1-4 alkyl group, (3) a hydroxy group or (4) $NH_2$ or (5) $R^{12}$ and $R^{13}$ together with the carbon atom to which they are attached may form a C3-7 carbocycle; and the arrow on the right hand side binds to —$CONR^6R^7$, —$SO_2R^8$ or —$COOR^9$, (3) a C2-4 alkenylene group, (4) a —O—C2-4 alkenylene group, (5) an oxygen atom or (6) a nitrogen atom which may be substituted with a C1-4 alkyl group;

$R^6$ and $R^7$ respectively and independently represent (1) a hydrogen atom, (2) a C1-4 alkyl group, (3) a C1-4 haloalkyl group, (4) a hydroxy group, (5) —$CONR^{15}R^{16}$, (6) —$SO_2NR^{15}R^{16}$, (7) —$COR^{17}$ or (8) —$SO_2R^{17}$, or $R^6$ and $R^7$ together with the nitrogen atom to which they are attached may form a 4- to 7-membered nitrogen-containing saturated heterocycle that may be substituted with a hydroxy group;

$R^8$ represents (1) a C1-4 alkyl group, (2) a C1-4 haloalkyl group or (3) $NR^{10}R^{11}$;

$R^9$ represents (1) a hydrogen atom or (2) a C1-8 alkyl group;

$R^{10}$ and $R^{11}$ respectively and independently represent (1) a hydrogen atom, (2) a C1-4 alkyl group, (3) —$CONR^{15}R^{16}$, (4) —$SO_2NR^{15}R^{16}$, (5) —$COR^{17}$ or (6) —$SO_2R^{17}$;

the ring 1 represents a 5- to 7-membered cyclic group;

$R^{15}$ and $R^{16}$ respectively and independently represent (1) a hydrogen atom, (2) a C1-4 alkyl group or (3) a 5- to 7-membered cyclic group;

$R^{17}$ represents (1) a C1-4 alkyl group or (2) a 5- to 7-membered cyclic group;

$M^1$ represents (1) a bond, (2) —C(O)—, (3) —O—, (4) —S—, (5) —C(O)O—, (6) —$CH_2O$— or (7) —C(O)NH—;

$M^2$ represents a halogen atom or a C1-4 haloalkyl group;

n represents an integer of 1 to 2;

m represents an integer of 1 to 2;

p represents an integer of 0 to 5;

r represents an integer of 0 to 4;

t represents an integer of 1 to 4;

when p is 2 or more, a plurality of $R^3$ groups may be the same or different;

when r is 2 or more, a plurality of $R^4$ groups may be the same or different; and when t is 2 or more, a plurality of $R^{12}$ and $R^{13}$ groups may be respectively the same or different;

a salt thereof, a solvate thereof, an N-oxide thereof or a prodrug thereof;

[2] the compound according to [1], wherein $R^1$ is (1) a C1-8 alkyl group which may be substituted with 1 to 5 $R^{21}$ groups, or (2) a C3-7 carbocycle which may be substituted with 1 to 5 substituents selected from the group consisting of a C1-4 alkyl group, a C1-4 haloalkyl group, a C1-4 alkoxy group and a halogen atom;

[3] the compound according to [1] or [2], wherein $M^1$ is (1) —O— or (2) —C(O)O—;

[4] the compound according to [1], which is represented by the general formula (I-1):

[C 6]

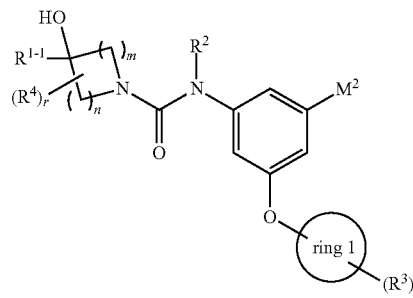

(I-1)

wherein $R^{1-1}$ represents (1) a C1-8 alkyl group which may be substituted with 1 to 5 $R^{21}$ groups, or (2) a C3-7 carbocycle which may be substituted with 1 to 5 substituents selected from the group consisting of a C1-4 alkyl group, a C1-4 haloalkyl group, a C1-4 alkoxy group and a halogen atom; and other symbols have the same meanings as above;

[5] the compound according to [4], wherein $R^2$ is a hydrogen atom;

[6] the compound according to [4] or [5], wherein the ring 1 is (1) a benzene, (2) cyclohexane or (3) pyridine ring;

[7] the compound according to [4], wherein the compound represented by the general formula (I-1) as described in [4] is 2-{3-[3-{[(3-cyclohexyl-3-hydroxy-1-pyrrolidinyl)carbonyl]amino}-5-(trifluoromethyl)phenoxy]phenyl}-2-methylpropanoic acid, 4-cyclopentyl-4-hydroxy-N-[3-{4-[(methylsulphonyl)carbamoyl]phenoxy}-5-(trifluoromethyl)phenyl]-1-piperidine carboxamide, 4-cyclopentyl-N-[3-{4-[(ethylsulphonyl)carbamoyl]phenoxy}-5-(trifluoromethyl)phenyl]-4-hydroxy-1-piperidine carboxamide, 1-{4-[3-{[(3-cyclohexyl-3-hydroxy-1-pyrrolidinyl)carbonyl]amino}-5-(trifluoromethyl)phenoxy]phenyl}cyclopropanecarboxylic acid, 2-{4-[3-{[(3-cyclohexyl-3-hydroxy-1-pyrrolidinyl)carbonyl]amino}-5-(trifluoromethyl)phenoxy]phenoxy}-2-methylpropanoic acid, 1-{4-[3-{[(3-cyclohexyl-3-hydroxy-1-pyrrolidinyl)carbonyl]amino}-5-(trifluoromethyl)phenoxy]phenoxy}cyclopropanecarboxylic acid, 1-{4-[3-{[(3-cyclohexyl-3-hydroxy-1-pyrrolidinyl)carbonyl]amino}-5-(trifluoromethyl)phenoxy]phenyl}cyclobutanecarboxylic acid, 1-{4-[3-{[(3-cyclohexyl-3-hydroxy-1-pyrrolidinyl)carbonyl]amino}-5-(trifluoromethyl)phenoxy]phenyl}cyclopentanecarboxylic acid, 3-{[(4-hydroxy-4-isobutyl-1-piperidinyl)carbonyl]amino}-5-(trifluoromethyl)benzoic acid, 2-(4-{[3-{[(4-hydroxy-4-isobutyl-1-piperidinyl)carbonyl]amino}-5-(trifluoromethyl)benzoyl]oxy}phenyl)-2-methylpropanoic acid, 1-{4-[3-chloro-5-({[4-(4-fluorophenyl)-4-hydroxy-1-piperidinyl]carbonyl}amino)phenoxy]phenoxy}cyclopropanecarboxylic acid or 2-[4-(3-fluoro-5-{[(4-hydroxy-4-isobutyl-1-piperidinyl)carbonyl]amino}phenoxy)phenyl]-2-methylpropanoic acid;
[8] the compound according to [4], wherein the compound represented by the general formula (I-1) as described in [4] is 4-cyclopentyl-4-hydroxy-N-[3-{4-[(methylsulphonyl)carbamoyl]phenoxy}-5-(trifluoromethyl)phenyl]-1-piperidine carboxamide or 1-{4-[3-{[(3-cyclohexyl-3-hydroxy-1-pyrrolidinyl)carbonyl]amino}-5-(trifluoromethyl)phenoxy]phenyl}cyclopentanecarboxylic acid;
[9] a pharmaceutical composition containing the compound represented by the general formula (I), the salt thereof, the solvate thereof, the N-oxide thereof or the prodrug thereof according to [1];
[10] the pharmaceutical composition according to [9], which is a S1P$_2$ antagonist;
[11] the pharmaceutical composition according to [9], which is a prophylactic and/or therapeutic agent for a S1P$_2$-mediated disease;
[12] the pharmaceutical composition according to [11], wherein the S1P$_2$-mediated disease is a disease resulting from vascular constriction, fibrosis, respiratory disease, arteriosclerosis, peripheral arterial occlusive disease, retinopathy, glaucoma, age-related macular degeneration, nephritis, diabetes, a diabetic complication, dyslipidemia, hepatitis, hepatic cirrhosis, hepatic failure, neuropathy, rheumatoid arthritis, wound, pain, urticaria, systemic lupus erythematosus (SLE) or cancer;
[13] the pharmaceutical composition according to [12], wherein the disease resulting from vascular constriction is cerebral vasospastic disease, cardiac vasospastic disease, coronary vasospastic disease, hypertension, pulmonary hypertension, myocardial infarction, angina, arrhythmia, atrial fibrillation, portal hypertension, varix, ascites, splenomegaly, hepatic encephalopathy or ischemia-reperfusion injury;
[14] the pharmaceutical composition according to [13], which is capable of persistently reducing portal pressure;
[15] the pharmaceutical composition according to [14], which can be administered once daily;
[16] the pharmaceutical composition according to any one of [13] to [15], which is a prophylactic agent for primary or secondary bleeding from esophageal varix associated with portal hypertension;
[17] a method for prophylaxis and/or therapy of a S1P$_2$-mediated disease, comprising administering an effective amount of the compound represented by the general formula (I), the salt thereof, the solvate thereof, the N-oxide thereof or the prodrug thereof according to [1] to a mammal;
[18] the compound represented by the general formula (I), the salt thereof, the solvate thereof, the N-oxide thereof or the prodrug thereof according to [1] for prophylaxis and/or therapy of a S1P$_2$-mediated disease; and
[19] use of the compound represented by the general formula (I), the salt thereof, the solvate thereof, the N-oxide thereof or the prodrug thereof according to [1] for producing a prophylactic and/or therapeutic agent for a S1P$_2$-mediated disease.

The present compound has high human S1P$_2$ antagonistic activity, and thus is useful for therapy of S1P$_2$-mediated diseases such as diseases resulting from vascular constriction and fibrosis.

BEST MODE FOR CARRYING OUT THE INVENTION

The present invention is described in detail hereinbelow.
The halogen atom as used herein means fluorine, chlorine, bromine and iodine.
The C1-8 alkyl group as used herein may include linear or branched C1-8 alkyl groups which may include, for example, methyl, ethyl, propyl, butyl, pentyl, hexyl, heptyl, octyl, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, 2,2-dimethylpropyl, 1-methylpentyl, 1-ethylbutyl, 2-ethylbutyl, 1-ethyl-1-methylpropyl, 1-ethyl-2-methylpropyl, 1,1-dimethylbutyl, 1,2-dimethylbutyl, 1,3-dimethylbutyl, 2-methylpentyl, 3-methylpentyl, 4-methylpentyl, 2,3-dimethylbutyl, 1-methylhexyl, 1-ethylpentyl, 2-ethylpentyl, 1-propylbutyl, 2-methyl-3-hexyl, 1,2-dimethylpentyl, 1,3-dimethylpentyl, 1,4-dimethylpentyl, 1-ethyl-1-methylbutyl, 1-methyl-2-ethylbutyl, 1-ethyl-2-methylbutyl, 1-ethyl-3-methylbutyl, 1,1-dimethylpentyl, 1,1,3-trimethylbutyl, 1,1-diethylpropyl, 2-methylhexyl, 3-methylhexyl, 4-methylhexyl, 5-methylhexyl, 3-ethylpentyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 1-propylpentyl, 2-propylpentyl, 1,5-dimethylhexyl, 1-ethyl-4-methylpentyl, 1-propyl-3-methylbutyl, 1,1-dimethylhexyl, 1-ethyl-1-methylpentyl and 1,1-diethylbutyl groups.

The C1-4 alkyl group as used herein may include linear or branched C1-4 alkyl groups which may include, for example, methyl, ethyl, propyl, butyl, isopropyl, isobutyl, sec-butyl and tert-butyl groups.

The C1-4 haloalkyl group as used herein means a fluoromethyl group, a chloromethyl group, a bromomethyl group, an iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group and a 4-bromobutyl group.

The C2-8 alkenyl group as used herein may include linear or branched C2-8 alkenyl groups which may include, for example, vinyl, propenyl, butenyl, pentenyl, hexenyl, hexadienyl, heptenyl, heptadienyl, octenyl, octadienyl, 2-methylpropen-1-yl, 2-ethyl-1-buten-1-yl, 2-methylbuten-2-yl and 2-methylpenten-2-yl groups.

The C2-4 alkenylene group as used herein may include ethenylene, propenylene and butenylene groups.

The C2-8 alkynyl group as used herein may include linear or branched C2-8 alkynyl groups which may include, for example, ethynyl, propynyl, butynyl, pentynyl, hexynyl, hexadiynyl, heptynyl, heptadiynyl, octynyl, octadiynyl and 3,3-dimethyl-1-butyn-1-yl groups.

The C1-4 alkoxy group as used herein may include, for example, methoxy, ethoxy, propoxy, isopropoxy, butoxy, isobutoxy, sec-butoxy and tert-butoxy groups.

The C3-7 carbocycle as used herein means a C3-7 monocyclic carbocycle or a C3-7 carbocycle which may be partially or fully saturated and may include, for example, cyclopropane, cyclobutane, cyclopentane, cyclohexane, cycloheptane, cyclobutene, cyclopentene, cyclohexene, cycloheptene, cyclobutadiene, cyclopentadiene, cyclohexadiene, cycloheptadiene and benzene rings.

The C5-7 carbocycle as used herein means a C5-7 monocyclic carbocycle or a C5-7 carbocycle which may be partially or fully saturated and may include, for example, cyclopentane, cyclohexane, cycloheptane, cyclopentene, cyclohexene, cycloheptene, cyclopentadiene, cyclohexadiene, cycloheptadiene and benzene rings.

The 4- to 7-membered nitrogen-containing saturated heterocycle as used herein refers to partially or fully saturated 4- to 7-membered monocyclic heterocycles which contain 1 to 5 hetero atoms selected from an oxygen atom, a nitrogen atom and a sulphur atom and inevitably contain one or more nitrogen atoms. For example, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisooxazole, tetrahydroisooxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine and thiomorpholine rings may be mentioned.

The 5- to 7-membered cyclic group as used herein means a C5-7 carbocycle and a 5- to 7-membered heterocycle. The C5-7 carbocycle has the same meaning as above and the 5- to 7-membered heterocycle may include 5- to 7-membered unsaturated heterocycles and 5- to 7-membered saturated heterocycles. The 5- to 7-membered heterocycles may include, for example, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiopehene, tetrahydrothiopehene, dihydrothiopyran, tetrahydrothiopyran, dihydrothiepine, tetrahydrothiepine, perhydrothiepine, dihydrooxazole, tetrahydrooxazole (oxazolidine), dihydroisooxazole, tetrahydroisooxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiopehene, thiopyran, thiepine, oxazole, isooxazole, thiazole, isothiazole, furazan, oxadiazole, oxazine, oxadiazine, oxazepine, oxadiazepine, thiadiazole, thiazine, thiadiazine, thiazepine and thiadiazepine rings.

In the present invention, $R^1$ is preferably a C1-8 alkyl group which may be substituted with 1 to 5 $R^{21}$ groups or a C5-7 carbocycle which may be substituted with 1 to 5 substituents selected from the group consisting of a C1-4 alkyl group, a C1-4 haloalkyl group, a C1-4 alkoxy group and a halogen atom, and more preferably a branched C1-8 alkyl group or a cyclopentane, cyclohexane or benzene ring which may be substituted with 1 to 5 substituents selected from the group consisting of a halogen atom and a trifluoromethyl group. The branched C1-8 alkyl group is preferably an isopropyl, isobutyl, 2-ethylbutyl, 2-methylpentyl or 3-methylpentyl group.

In the present invention, $R^{21}$ is preferably a fluorine atom.

In the present invention, $R^2$ is preferably a hydrogen atom.

In the present invention, $R^3$ is preferably -L-CONR$^6$R$^7$, -L-SO$_2$R$^8$ or -L-COOR$^9$.

In the present invention, $M^1$ is preferably —O— or —C(O)O—.

In the present invention, $M^2$ is preferably a fluorine atom, a chorine atom or a C1-4 haloalkyl group, more preferably a C1-4 haloalkyl group, and the C1-4 haloalkyl group is preferably a fluoromethyl group, a difluoromethyl group or a trifluoromethyl group.

In the present invention, the ring 1 is preferably a benzene, pyridazine, pyrimidine, pyrazine, pyridine or cyclohexane ring and more preferably a benzene ring.

In the present invention, the compound represented by the general formula (I) is preferably a compound represented by the general formula (I-1):

[C 7]

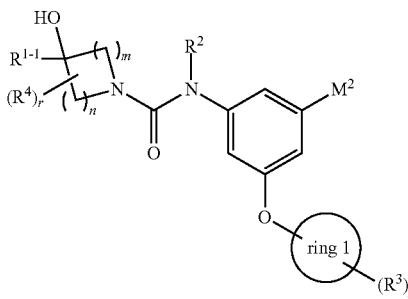

(I-1)

wherein all the symbols have the same meanings as above. In the general formula (I-1), $R^2$ is preferably a hydrogen atom; $R^3$ is preferably -L-CONR$^6$R$^7$, -L-SO$_2$R$^8$ or -L-COOR$^9$ and more preferably -L-CONR$^6$R$^7$ or -L-COOR$^9$; $M^2$ is preferably a fluoromethyl group, a difluoromethyl group or a trifluoromethyl group and more preferably a trifluoromethyl group; the ring 1 is preferably a benzene, pyridine or cyclohexane ring and the ring 1 is more preferably a benzene ring.

In the present invention, the compound represented by the general formula (I) is preferably a compound represented by the general formula (I-1):

[C 8]

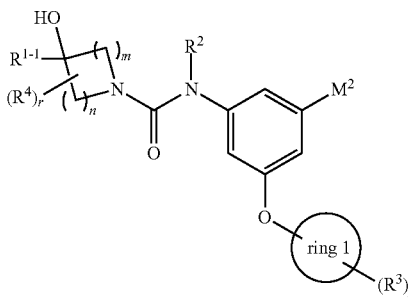

(I-1)

wherein all the symbols have the same meanings as above. In the general formula (I-1), $R^2$ is preferably a hydrogen atom; $R^3$ is preferably -L-CONR$^6$R$^7$, -L-SO$_2$R$^8$ or -L-COOR$^9$ and more preferably -L-CONR$^6$R$^7$ or -L-COOR$^9$; $M^2$ is preferably a C1-4 haloalkyl group; the C1-4 haloalkyl group is more preferably a fluoromethyl group, a difluoromethyl group or a trifluoromethyl group; the ring 1 is preferably a benzene, pyridine or cyclohexane ring and more preferably a benzene ring.

In the present invention, the compounds described in Examples are more preferred and 4-cyclopentyl-4-hydroxy-N-[3-{4-[(methylsulphonyl)carbamoyl]phenoxy}-5-(trifluoromethyl)phenyl]-1-piperidine carboxamide, or 1-{4-[3-{[(3-cyclohexyl-3-hydroxy-1-pyrrolidinyl)carbonyl]amino}-5-(trifluoromethyl)phenoxy]phenyl}cyclopentanecarboxylic acid is particularly preferred.

[Isomers]

The present invention encompasses all isomers unless particularly stated. For example, the alkyl group includes linear and branched groups. Moreover, the present invention encompasses geometrical isomers for double bonds, rings and condensed rings (E-forms, Z-forms, cis forms and trans forms), optical isomers due to asymmetrical carbon atoms (R and S forms, α and β configurations, enantiomers and diastereomers), optically active substances having optical rotating activity (D, L, d and l forms), polar substances which can be separated by chromatography (high polarity substances and low polarity substances), equilibrium compounds, rotamers, mixtures thereof at arbitrary proportions and racemic mixtures. The present invention also encompasses tautomers.

The optical isomers according to the present invention may include not only the ones with 100% purity but also the ones containing other optical isomers at less than 50%.

In the present invention, unless particularly stated, the symbol:

[C 9]

indicates that the bond projects below the plane of the paper (i.e. α configuration), the symbol:

[C 10]

indicates that the bond projects above the plane of the paper (i.e. β configuration), and the symbol:

[C 11]

indicates that the bond is the α configuration, the β configuration or the mixture of these configurations at arbitrary proportions, as apparent to a person skilled in the art.

The compound represented by the general formula (I) is converted to a salt by the well-known method. The salt is preferably water-soluble. Appropriate salts may include alkali metal (potassium, sodium and the like) salts, alkaline earth metal (calcium, magnesium and the like) salts, ammonium salts, pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine and the like) salts, acid addition salts (inorganic acid salts (hydrochlorides, hydrobromides, hydroiodides, sulphates, phosphates, nitrates and the like), organic acid salts (acetates, trifluoroacetates, lactates, tartrates, oxalates, fumarates, maleates, benzoates, citrates, methanesulphonates, ethanesulphonates, benzenesulphonates, toluenesulphonates, isethionates, glucuronates, gluconates and the like) and the like) and the like.

The compound represented by the general formula (I) and the salt thereof can also be converted to a solvate. The solvate preferably has low toxicity and is water-soluble. Appropriate solvates may include, for example, solvates with water and alcoholic solvents (e.g. ethanol).

The N-oxide of the compound represented by the general formula (I) refers to the compound represented by the general formula (I) in which the nitrogen atom is oxidized. The N-oxide of the compound represented by the general formula (I) may also be the alkali (alkaline earth) metal salt, the ammonium salt, the organic amine salt and the acid addition salt as described above.

The prodrug of the compound represented by the general formula (I) refers to a compound which is converted in vivo to the compound represented by the general formula (I) by the reaction with enzymes, gastric acid and the like. The prodrug of the compound represented by the general formula (I) may include, when the compound represented by the general formula (I) has a hydroxy group, compounds in which the hydroxy group is acylated, alkylated, phosphorylated or converted to borate (e.g. the present compounds in which the hydroxy group is converted to acetyl, palmitoyl, propanoyl, pivaloyl, succinyl, fumaryl, alanyl, dimethylaminomethylcarbonyl or the like); compounds represented by the general formula (I) in which the carboxyl group is esterified or amidated (e.g. compounds represented by the general formula (I) in which the carboxyl group is converted to ethyl ester, isopropyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methylamide or the like) and the like. These compounds can be produced by the well-known methods. The prodrug of the compound represented by the general formula (I) may be hydrates or non-hydrates. The prodrug of the compound represented by the general formula (I) may be the one which is converted to the compound represented by the general formula (I) under the physiological condition such as those disclosed in "Iyakuhin no Kaihatsu", vol. 7 "Bunshi Sekkei", p. 163-198, 1990, Hirokawa Shoten Co. The compound represented by the general formula (I) may be labelled with an isotope (for example, $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$ and the like).

[Production Method of the Present Compound]

The present compound can be produced by well-known methods, for example, the method described in Comprehensive Organic Transformations: A Guide to Functional Group Preparations, 2nd Edition (Richard C. Larock, John Wiley & Sons Inc, 1999) or the method described in Examples with appropriate modifications and combinations.

The compound of the general formula (I), wherein $R^2$ is a hydrogen atom and $M^1$ is an oxygen atom, namely the compound represented by the general formula (I-A):

[C 12]

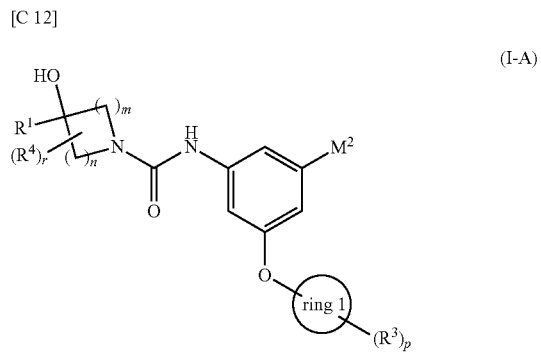

(I-A)

wherein all the symbols have the same meanings as above, can be produced by the reaction scheme 1 as follows:

Reaction scheme 1

[C 13]

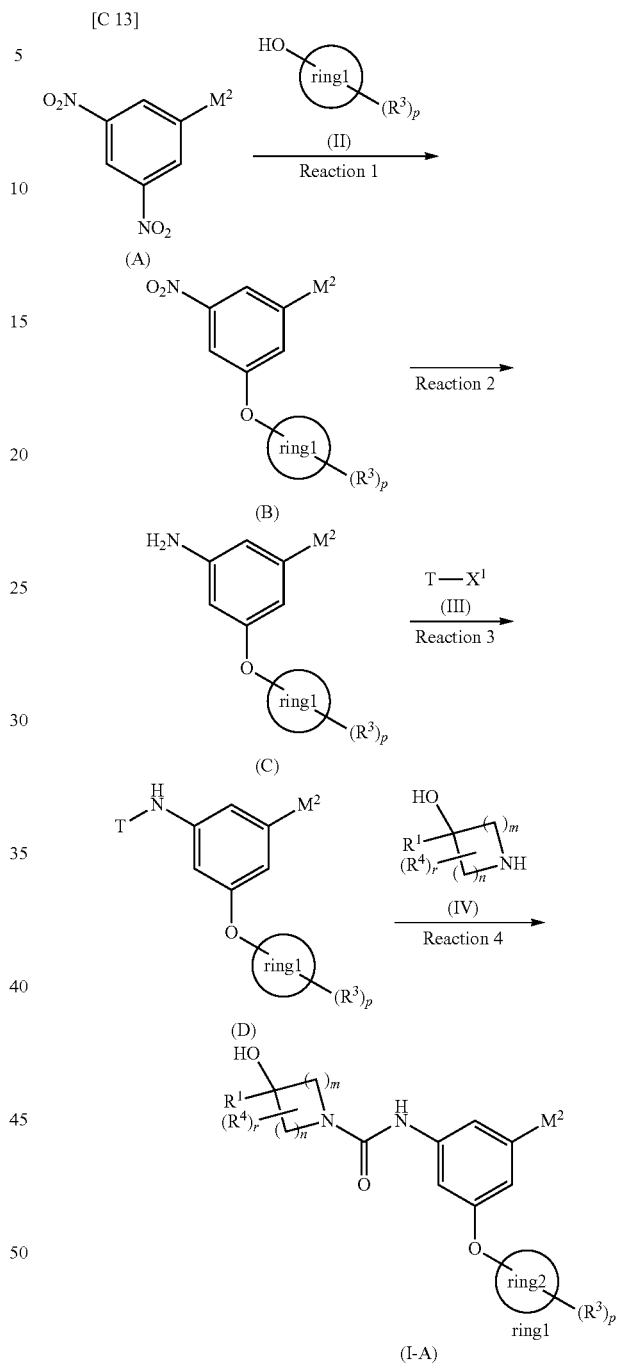

(I-A)

wherein T represents a protecting group of the amino group having the carbonyl group (e.g. a 2,2,2-trichloroethoxycarbonyl (Troc) group, a phenoxycarbonyl group, a p-nitrophenoxycarbonyl group and the like); $X^1$ represents a halogen atom; and other symbols have the same meanings as above.

In the reaction step formula 1, the reaction 1 can be carried out as an etherification reaction between the compound represented by the general formula (A) and the compound represented by the general formula (II). This etherification reaction is well known and is carried out, for example, in an organic solvent (N,N-dimethylacetamide, N,N-dimethylformamide, dimethyl sulphoxide, chloroform, dichloromethane, diethyl ether, tetrahydrofuran, methyl t-butyl ether and the like), in the presence of an alkali metal hydroxide (sodium hydroxide, potassium hydroxide, lithium hydroxide and the like), an alkali metal hydride (sodium hydride and the like), an alkaline earth metal hydroxide (barium hydroxide, calcium hydroxide and the like), a phosphate (potassium phosphate and the like) or a carbonate (cesium carbonate, sodium carbonate, potassium carbonate and the like) or an aqueous solution thereof or a mixture thereof and at 0 to 100° C.

In the reaction step formula 1, the reaction 2 can be carried out as a reduction reaction of the nitro group of the compound represented by the general formula (B). The reduction reaction of the nitro group is well known and is carried out, for example, by the methods described hereinbelow.

(1) The reaction is carried out, for example, in a solvent [ethers (tetrahydrofuran, dioxane, dimethoxyethane, diethyl ether and the like), alcohols (methanol, ethanol and the like), benzenes (benzene, toluene and the like), ketones (acetone, methyl ethyl ketone and the like), nitriles (acetonitrile and the like), amides (dimethylformamide and the like), water, ethyl acetate, acetic acid or mixed solvents of two or more of the above], in the presence of a hydrogenation catalyst (palladium-carbon, palladium black, palladium, palladium hydroxide, platinum dioxide, platinum-carbon, nickel, Raney nickel, ruthenium chloride and the like), in the presence or absence of an acid (hydrochloric acid, sulphuric acid, hypochlorous acid, boric acid, tetrafluoroboric acid, acetic acid, p-toluenesulphonic acid, oxalic acid, trifluoroacetic acid, formic acid and the like), in an hydrogen atmosphere of normal or increased pressure, in the presence of ammonium formate or hydrazine and at a temperature of 0 to 200° C.

(2) The reaction is carried out, for example, in a water-miscible solvent (ethanol, methanol, tetrahydrofuran and the like), in the presence or absence of an acid (hydrochloric acid, hydrobromic acid, ammonium chloride, acetic acid, ammonium formate and the like), by using a metal reagent (zinc, iron, tin, tin chloride, iron chloride, samarium, indium, sodium borohydride-nickel chloride and the like) at a temperature of 0 to 150° C.

In the reaction step formula 1, the reaction 3 is well known and is carried out with the compound represented by the general formula (C) and the compound represented by the general formula (III), for example, by reaction of the compound represented by the general formula (III) in the presence of a base (pyridine, triethylamine, dimethylaniline, dimethylaminopyridine, diisopropylethylamine and the like) with the compound represented by the general formula (C) in an organic solvent (chloroform, dichloromethane, diethyl ether, tetrahydrofuran and the like) at a temperature of 0 to 40° C. The compound represented by the general formula (III) can also be subjected to the reaction with the general formula (C) in an organic solvent (ethyl acetate, dioxane, tetrahydrofuran and the like), with using an alkaline aqueous solution (sodium hydrogen carbonate solution, sodium hydroxide solution and the like) at 0 to 40° C.

In the reaction step formula 1, the reaction 4 is well known and is carried out with the compound represented by the general formula (D) and the compound represented by the general formula (IV), for example, by reaction of the compound represented by the general formula (D) in the presence of a base (pyridine, triethylamine, dimethylaniline, dimethylaminopyridine, diisopropylethylamine and the like) with the compound represented by the general formula (IV) in an organic solvent (N,N-dimethylacetamide, chloroform, dichloromethane, diethyl ether, tetrahydrofuran and the like) at a temperature of 0° C. to a reflux temperature.

In the reaction step formula 1, when the compound represented by the general formula has a protecting group, for example, when $R^3$ is protected, deprotection reaction may be carried out if necessary. Deprotection reaction of protecting groups is well known and can be carried out by following methods which may include, for example, (1) deprotection reaction by alkaline hydrolysis, (2) deprotection reaction under acidic conditions, (3) deprotection reaction by hydrolysis, (4) deprotection reaction of silyl groups, (5) deprotection reaction using a metal, (6) deprotection reaction using a metal complex and the like.

These methods are specifically described hereinbelow.

(1) Deprotection reaction by alkaline hydrolysis is carried out, for example, in an organic solvent (e.g. methanol, tetrahydrofuran and dioxane), by using an alkali metal hydroxide (e.g. sodium hydroxide, potassium hydroxide and lithium hydroxide), an alkaline earth metal hydroxide (e.g. barium hydroxide and calcium hydroxide) or a carbonate (e.g. sodium carbonate and potassium carbonate) or an aqueous solution thereof or a mixture thereof at 0 to 40° C.

(2) Deprotection reaction under acidic conditions is carried out, for example, in an organic solvent (e.g. dichloromethane, chloroform, dioxane, ethyl acetate, methanol, isopropyl alcohol, tetrahydrofuran and anisole) and in an organic acid (e.g. acetic acid, trifluoroacetic acid, methanesulphonic acid and p-tosylic acid) or an inorganic acid (e.g. hydrochloric acid and sulphuric acid) or a mixture thereof (e.g. hydrogen bromide/acetic acid) in the presence or absence of 2,2,2-trifluoroethanol at 0 to 100° C.

(3) Deprotection reaction by hydrolysis is carried out, for example, in a solvent (e.g. ethers (e.g. tetrahydrofuran, dioxane, dimethoxyethane and diethyl ether), alcohols (e.g. methanol and ethanol), benzenes (e.g. benzene and toluene), ketones (e.g. acetone and methyl ethyl ketone), nitriles (e.g. acetonitrile), amides (e.g. N,N-dimethylformamide), water, ethyl acetate, acetic acid or mixed solvents of two or more of the above), in the presence of a catalyst (e.g. palladium-carbon, palladium black, palladium hydroxide-carbon, platinum oxide and Raney nickel), in a hydrogen atmosphere of normal or increased pressure or in the presence of ammonium formate at 0 to 200° C.

(4) Deprotection reaction of silyl groups is carried out, for example, in a water-miscible organic solvent (e.g. tetrahydrofuran and acetonitrile), by using tetrabutylammonium fluoride at 0 to 40° C. Alternatively, the reaction is carried out, for example, in an organic acid (e.g. acetic acid, trifluoroacetic acid, methanesulphonic acid and p-tosylic acid) or an inorganic acid (e.g. hydrochloric acid and sulphuric acid) or a mixture thereof (e.g. hydrogen bromide/acetic acid) at −10 to 100° C.

(5) Deprotection reaction using a metal is carried out, for example, in an acidic solvent (e.g. acetic acid, a buffer of pH 4.2 to 7.2 or a mixed solution thereof with an organic solvent such as tetrahydrofuran) in the presence of zinc powder with application of ultrasonic, if necessary, at 0 to 40° C.

(6) Deprotection reaction using a metal complex is carried out, for example, in an organic solvent (e.g. dichloromethane, N,N-dimethylformamide, tetrahydrofuran, ethyl acetate, acetonitrile, dioxane and ethanol), water or a mixed solvent thereof in the presence of a trap reagent (e.g. tributyltin hydride, triethylsilane, dimedone, morpholine, diethylamine and pyrrolidine), in the presence of an organic acid (e.g. acetic acid, formic acid and 2-ethylhexanoic acid) and/or a salt of an organic acid (e.g. sodium 2-ethylhexanoate and potassium 2-ethylhexanoate), in the presence or absence of a phosphine reagent (e.g. triphenylphosphine), with using a metal complex (e.g. tetrakis triphenylphosphine palladium (0), bis(triphenylphosphine)palladium (II) dichloride, palladium (II) acetate and tris(triphenylphosphine) rhodium (I) chloride) at 0 to 40° C.

Alternatively, the deprotection reaction can be carried out by the method described in, for example, T. W. Greene, Protective Groups in Organic Synthesis, Wiley, New York, 1999.

The protecting group of a hydroxy group may include, for example, a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group and the like.

The protecting group of an amino group may include, for example, a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, a 2-(trimethylsilyl)ethoxymethyl (SEM) group and the like.

The protecting group of a hydroxy group and an amino group is not particularly limited to those mentioned above as far as it can be readily and selectively eliminated. For example, the ones described in T. W. Greene, Protective Groups in Organic Synthesis, Wiley, New York, 1999 may be used.

In the reactions described herein, the compounds used as starting materials such as the compounds represented by the general formulae (A), (II), (III), and (IV) are well known or can be readily produced according to well-known methods.

In the reactions described herein, reactions accompanied by heating can be carried out, as apparent to a person skilled in the art, with a water bath, an oil bath, a sand bath or a microwave.

In the reactions described herein, a solid phase immobilized reagent which is immobilized on a high molecular polymer (e.g. polystyrene, polyacrylamide, polypropylene and polyethylene glycol) may be used.

In the reactions described herein, reaction products can be purified according to a conventional purification means such as distillation at normal or reduced pressure, high performance liquid chromatography using silica gel or magnesium silicate, thin layer chromatography, ion exchange resins, scavenger resins or column chromatography or washing and re-crystallization. Purification can be carried out after each reaction or after a few reactions.

[Toxicity]

The present compound has sufficiently low toxicity and thus can be used safely as a medicament.

[Pharmaceutical Application]

The compound of the present invention has $S1P_2$ (EDG-5) antagonistic activity and thus is useful as a prophylactic and/or therapeutic agent for a $S1P_2$-mediated disease. The $S1P_2$-mediated disease may include a disease resulting from vascular constriction, fibrosis, respiratory disease, arteriosclerosis, peripheral arterial occlusive disease, retinopathy, glaucoma, age-related macular degeneration, nephritis, diabetes, a diabetic complication (including diabetic retinopathy, diabetic nephropathy and the like), dyslipidemia, hepatitis, hepatic cirrhosis, hepatic failure (including non-alcoholic steatohepatitis, alcoholic steatohepatitis, viral hepatitis and the like), neuropathy, rheumatoid arthritis, wound, pain, urticaria, systemic lupus erythematosus (SLE), cancer and the like.

In the present invention, the disease resulting from vascular constriction may include cerebral vasospastic disease, cardiac vasospastic disease, coronary vasospastic disease, hypertension, pulmonary hypertension, myocardial infarction, angina, arrhythmia, atrial fibrillation, portal hypertension, varix, ascites, splenomegaly, hepatic encephalopathy, ischemia-reperfusion injury and the like.

The fibrosis as used herein may include pulmonary fibrosis, hepatic fibrosis, kidney fibrosis, myocardial fibrosis, skin fibrosis and the like.

The respiratory disease as used herein may include bronchial asthma, acute lung injury, sepsis, chronic obstructive pulmonary disease and the like.

In the present invention, varix may include esophageal varix, gastric varix, duodenal varix, enteric varix, colonic varix, rectal varix and the like.

The present compound is capable of reducing portal pressure and thus can be used as a prophylactic and/or therapeutic agent for portal hypertension and as a prophylactic agent for primary or secondary bleeding from esophageal varix associated with portal hypertension.

The present compound is capable of persistently reducing portal pressure and thus can exhibit the prophylactic and/or therapeutic effect of portal hypertension with administration of once daily.

The present compound may be combined with another drug so as to be administered as a concomitant drug in order to:

1) complement and/or enhance the prophylactic and/or therapeutic effect of the present compound;
2) improve kinetics and uptake and reduce the dosage of the present compound; and/or
3) decrease side effect of the present compound.

The concomitant drug of the present compound and another drug may be administered as a combined agent containing both components in one formulation or administered separately. This separate administration includes simultaneous administration and sequential administration. The sequential administration may include the administration of the present compound prior to another drug and the administration of another drug prior to the present compound. The manners of administration of the components may be the same or different.

The concomitant drug may exhibit prophylactic and/or therapeutic effect for any diseases without limitation as far as the prophylactic and/or therapeutic effect of the present compound is complemented and/or enhanced.

Another drug which is used for complementation and/or enhancement of the prophylactic and/or therapeutic effect of the present compound for the disease resulting from vascular constriction may include, for example, calcium antagonists, thrombolytic agents, thromboxane synthase inhibitors, endothelin antagonists, antioxidants, radical scavengers, PARP inhibitors, astrocyte function improving agents, Rho kinase inhibitors, angiotensin II antagonists, angiotensin-converting enzyme inhibitors, diuretic agents, phosphodiesterase (PDE) 4 inhibitors, prostaglandins (hereinafter sometimes abbreviated as PG or PGs), aldosterone antagonists, endothelin antagonists, prostacyclin formulations, nitrates, β-blockers, vasodilators and the like.

Another drug which is used for complementation and/or enhancement of the prophylactic and/or therapeutic effect of the present compound for fibrosis may include, for example, steroids, immunosuppressants, TGF-β inhibitors, PDE5 inhibitors and the like.

Another drug which is used for complementation and/or enhancement of the prophylactic and/or therapeutic effect of the present compound for the respiratory disease may include, for example, PDE4 inhibitors, steroids, β-agonists, leukotriene receptor antagonists, thromboxane synthase inhibitors, thromboxane A2 receptor antagonists, mediator release suppressing agents, antihistamines, xanthine derivatives, anticholinergic agents, cytokine inhibitors, PGs, forskolin formulations, elastase inhibitors, metalloprotease inhibitors, expectorants, antibiotics and the like.

The calcium antagonists may include, for example, nifedipine, benidipine hydrochloride, diltiazem hydrochloride, verapamil hydrochloride, nisoldipine, nitrendipine, bepridil hydrochloride, amlodipine besylate, lomerizine hydrochloride, efonidipine hydrochloride and the like. The thrombolytic agents may include, for example, alteplase, urokinase, tisokinase, nasaruplase, nateplase, tissue plasminogen activator, pamiteplase, monteplase and the like. The thromboxane synthase inhibitors may include, for example, ozagrel hydrochloride, imitrodast sodium and the like. The radical scavengers may include, for example, Radicut and the like. The PARP inhibitors may include, for example, 3-aminobenzamide, 1,3,7-trimethylxanthine, PD-141076, PD-141703 and the like.

The astrocyte function improving agents may include, for example, ONO-2506 and the like.

The Rho kinase inhibitors may include, for example, fasudil hydrochloride and the like.

The angiotensin II antagonists may include, for example, losartan, candesartan, valsartan, irbesartan, olmesartan, telmisartan and the like.

The angiotensin-converting enzyme inhibitors may include, for example, alacepril, imidapril hydrochloride, quinapril hydrochloride, temocapril hydrochloride, delapril hydrochloride, benazepril hydrochloride, captopril, trandolapril, perindopril erbumine, enalapril maleate, lisinopril and the like.

The diuretic agents may include, for example, mannitol, furosemide, acetazolamide, dichlorphenamide, methazolamide, trichlormethiazide, mefruside, spironolactone, aminophyline and the like.

The PDE4 inhibitors may include, for example, rolipram, cilomilast, Bay19-8004, NIK-616, roflumilast, cipamfylline, atizoram, SCH-351591, YM-976, V-11294A, PD-168787, ONO-6126, D-4396, IC-485 and the like.

The prostaglandins (PGs) may include, for example, PG receptor agonists, PG receptor antagonists and the like.

The PG receptor may include, for example, PGE receptors (EP1, EP2, EP3 and EP4), PGD receptors (DP and CRTH2), a PGF receptor (FP), a PGI receptor (IP), a thromboxane receptor (TP) and the like.

The aldosterone antagonists may include, for example, drospirenone, metyrapone, canrenoate potassium, canrenone, eplerenone, ZK-91587 and the like.

The prostacyclin formulations may include, for example, treprostinil sodium, epoprostenol sodium, beraprost sodium and the like.

The nitrates may include, for example, amyl nitrite, nitroglycerin, isosorbide dinitrate and the like.

The β-blockers may include, for example, alprenolol hydrochloride, bupranolol hydrochloride, bufetolol hydrochloride, oxprenolol hydrochloride, atenolol, bisoprolol fumarate, betaxolol hydrochloride, bevantolol hydrochloride, metoprolol tartrate, acebutolol hydrochloride, celiprolol hydrochloride, nipradilol, tilisolol hydrochloride, nadorol, propranolol hydrochloride, indenolol hydrochloride, carteolol hydrochloride, pindolol, bunitrolol hydrochloride, landiolol hydrochloride, esmolol hydrochloride, arotinolol hydrochloride, carvedilol, timolol maleate and the like.

The vasodilators may include, for example, diltiazem hydrochloride, trimetazidine hydrochloride, dipyridamole, etanofen hydrochloride, dilazep hydrochloride, trapidil, nicorandil and the like.

The steroids may include, as agents for oral administration or injection, for example cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone diacetate, triamcinolone acetonide, dexamethasone, dexamethasone acetate, dexamethasone sodium phosphate, dexamethasone palmitate, paramethasone acetate, betamethasone and the like. The steroids for inhalation may include, for example, beclomethasone propionate, fluticasone propionate, budesonide, flunisolide, triamcinolone, ST-126P, ciclesonide, dexamethasone palomithionate, mometasone furonate, prasterone sulphonate, deflazacort, methylprednisolone sleptanate, methylprednisolone sodium succinate and the like.

The immunosuppressants may include, for example, azathioprine, mizoribine, methotrexate, mycophenolate mofetil, cyclophosphamide, cyclosporine A, tacrolimus, sirolimus, everolimus, prednisolone, methylprednisolone, orthoclone OKT3, anti-human lymphocyte globulin, deoxyspergualin and the like.

The PDE5 inhibitors may include, for example, sildenafil, tadalafil, vardenafil, udenafil and the like.

The β agonists may include, for example, fenoterol hydrobromide, salbutamol sulphate, terbutaline sulphate, formoterol fumarate, salmeterol xinafoate, isoproterenol sulphate, orciprenaline sulphate, clorprenaline sulphate, epinephrine, trimetoquinol hydrochloride, hexoprenaline sulphate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meluadrine tartrate, AR-C68397, levosalbutamol, R,R-formoterol, KUR-1246, KUL-7211, AR-C89855, S-1319 and the like.

The leukotriene receptor antagonists may include, for example, pranlukast hydrate, montelukast, zafirlukast, seratrodast and the like.

The thromboxane A2 receptor antagonists may include, for example, seratrodast, ramatroban, domitroban calcium hydrate and the like.

The mediator release suppressing agents may include, for example, tranilast, cromolyn sodium, amlexanox, repirinast, ibudilast, tazanolast, pemirolast potassium and the like.

The antihistamines may include, for example, ketotifen fumarate, mequitazine, azelastine hydrochloride, oxatomide, terfenadine, emedastine fumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andolast, auranofin, acrivastine and the like.

The xanthine derivatives may include, for example, aminophylline, theophylline, doxofylline, cipamfylline, diprophylline and the like.

The anticholinergic agents may include, for example, ipratropium bromide, oxytropium bromide, flutropium bromide, cimetropium bromide, temiverine, tiotropium bromide, revatropate and the like.

The cytokine inhibitors may include, for example, suplatast tosilate and the like.

The elastase inhibitors may include, for example, ONO-5046, ONO-6818, MR-889, PBI-1101, EPI-HNE-4, R-665 and the like.

The expectorants may include, for example, foeniculated ammonia spirit, sodium hydrogen carbonate, bromhexine hydrochloride, carbocysteine, ambroxol hydrochloride, ambroxol hydrochloride sustained release preparation, methylcysteine hydrochloride, acetylcysteine, L-ethylcysteine hydrochloride, tyloxapol and the like.

The antibiotics may include, for example, cefuroxime sodium, meropenem trihydrate, netilmicin sulphate, sisomicin sulphate, ceftibuten, PA-1806, IB-367, tobramycin, PA-1420, doxorubicin, astromicin sulphate, cefetamet pivoxil hydrochloride and the like. The antibiotics for inhalation may include, for example, PA-1806, IB-367, tobramycin, PA-1420, doxorubicin, astromicin sulphate, cefetamet pivoxil hydrochloride and the like.

The drug which is combined with the present compound encompasses not only the known compounds but also the compounds which will be found in future.

The present compound is usually administered systemically or locally in an oral or parenteral form. Oral formulations may include, for example, liquids for oral administration (e.g. elixirs, syrups, pharmaceutically acceptable solutions, suspensions and emulsions), solid agents for oral administration (e.g. tablets (including sublingual tablets and oral disintegration tablets), pills, capsules (including hard capsules, soft capsules, gelatine capsules and microcapsules), powders, granules and troches) and the like. Parenteral formulations may include, for example, liquids (e.g. injections (subcutaneous injections, intravenous injections, intramuscular injections, intraperitoneal injections, infusions and the like), ophthalmic solutions (e.g. aqueous ophthalmic solutions (aqueous ophthalmic solutions, aqueous ophthalmic suspensions, viscous ophthalmic solutions and solubilized ophthalmic solutions), non-aqueous ophthalmic solutions (non-aqueous ophthalmic solutions, non-aqueous ophthalmic suspensions and the like)) and the like), topical formulations (e.g. ointments (ophthalmic ointments and the like)), eardrops and the like. These formulations may be controlled-release preparations such as prompt release preparations or sustained release preparations. These formulations can be produced according to well-known methods such as the method described in Japanese Pharmacopoeia and the like.

The liquids for oral administration are produced by, for example, dissolving, suspending or emulsifying the active ingredient in a diluent that is generally used (e.g. purified water, ethanol and a mixture thereof). The liquids may further contain a wetting agent, a suspending agent, an emulsifying agent, a sweetening agent, a flavouring agent, an aroma, a preservative, a buffering agent and the like.

The solids for oral administration are formulated according to conventional methods by, for example, mixing the active ingredient with a vehicle (e.g. lactose, mannitol, glucose, microcrystalline cellulose and starch), a binder (e.g. hydroxypropyl cellulose, polyvinylpyrrolidone and magnesium aluminometasilicate), a disintegrant (e.g. calcium carboxymethyl cellulose), a lubricant (e.g. magnesium stearate), a stabiliser, a solution adjuvant (glutamic acid, aspartic acid and the like) and the like. The solids may be, if desired, coated with a coating agent (e.g. sucrose, gelatine, hydroxypropyl cellulose and hydroxypropyl methylcellulose phthalate) and may be coated with two or more layers.

The topical formulations as parenteral formulations are produced according to well-known methods or conventional formulations. For example, ointments are produced by triturating or melting the active ingredient in a base. The base for ointments is selected among those well-known or conventionally used. One or more selected from the followings, for example, may be used solely or in combination: a higher fatty acid or higher fatty acid ester (e.g. adipic acid, myristic acid, palmitic acid, stearic acid, oleic acid, adipate ester, myristate ester, palmitate ester, stearate ester and oleate ester), a wax (e.g. beeswax, whale wax and ceresin), a surfactant (e.g. polyoxyethylene alkyl ether phosphate esters), a higher alcohol (e.g. cetanol, stearyl alcohol and cetostearyl alcohol), a silicone oil (e.g. dimethylpolysiloxane), a hydrocarbon (e.g. hydrophilic petrolatum, white petrolatum, purified lanolin and liquid paraffin), a glycol (e.g. ethylene glycol, diethylene glycol, propylene glycol, polyethylene glycol and macrogol), vegetable oil (e.g. castor oil, olive oil, sesame oil and turpentine oil), animal oil (e.g. mink oil, egg-yolk oil, squalane and squalene), water, an absorption enhancing agent and a rash preventing agent. The formulations may further contain a humectant, a preservative, a stabilizer, an antioxidant, an aroma conferring agent and the like.

The injections as parenteral formulations encompass solutions, suspensions, emulsions and solid injections which are dissolved or suspended in a solvent upon use. The injections are used by, for example, dissolving, suspending or emulsifying the active ingredient in a solvent. The solvent used is, for example, distilled water for injections, saline, vegetable oil, propylene glycol, polyethylene glycol, alcohols such as ethanol or a combination thereof. The injections may further contain a stabilizer, a solution adjuvant (e.g. glutamic acid, aspartic acid and Polysolvate 80®), a suspending agent, an emulsifying agent, a soothing agent, a buffering agent, a preservative and the like. The injections are produced by sterilization at the final stage or through an aseptic manipulation. Alternatively, aseptic solid formulations, for example freeze-dried formulations, may be produced which may be dissolved, before use, in sterilized or aseptic distilled water for injection or another solvent.

For the purposes described above, the present compound or a concomitant agent of the present compound and another drug is generally administered systemically or locally in an oral or parenteral form. The dosage may vary according to the age, weight, symptoms, therapeutic effect, the manner of administration, treatment period and the like, and may be generally administered orally at a single dose for an adult of from 1 ng to 1000 mg with one or a few times daily, or administered parenterally at a single dose for an adult of from 0.1 ng to 10 mg with one or a few times daily, or continuously administered intravenously for 1 hour to 24 hours daily. The dosage may vary, as described above, according to various conditions, of course, and thus the dosage which is less than the range described above may be sufficient in some cases and the dosage which is more than the range described above may be required in some cases.

EXAMPLES

The present invention is hereinbelow described in detail by way of Examples which do not limit the present invention.

The solvents described in brackets in the sections of chromatography separation and TLC indicate the elution solvents or developing solvents used and the proportions are represented by volume ratios.

The solvents described in brackets in the sections of NMR indicate the solvents used for the measurements.

The compounds are denominated in the present specification by using a computer programme, ACD/Name® from Advanced Chemistry Development which generally denominates according to the rules from IUPAC, or according to the IUPAC nomenclature system.

Experimental Examples

Example 1: Benzyl 2-methyl-2-{3-[3-nitro-5-(trifluoromethyl)phenoxy]phenyl}propanoate

[C 14]

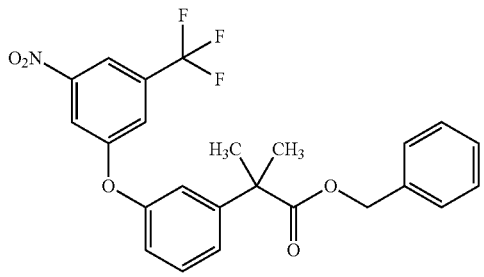

Under an argon atmosphere, 1,3-dinitro-5-(trifluoromethyl)benzene (1.52 g) and benzyl 2-(3-hydroxyphenyl)-2-methylpropanoate (1.735 g) were added to dimethylformamide (DMF) (10 mL) at room temperature and potassium sulphate (2.04 g) was added to the mixture followed by stirring at 90° C. for 9 hours. The reaction solution was cooled to room temperature, diluted with ethyl acetate, washed twice with water, washed with a brine and dried over anhydrous magnesium sulphate and the solvent was distilled off. The resulting residue was purified by silica gel chromatography (hexane:ethyl acetate=100:0→0:100) to give the titled compound (2.82 g) having the following physical properties.

$^1$H-NMR (CDCl$_3$): δ 8.18-6.80, 5.12, 1.62.

Example 2: Benzyl 2-{3-[3-amino-5-(trifluoromethyl)phenoxy]phenyl}-2-methylpropanoate

[C 15]

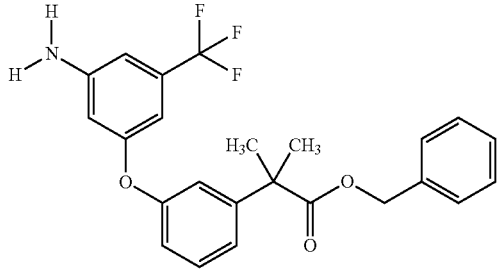

The compound (2.82 g) produced in Example 1 was dissolved in ethanol (50 mL) and water (10 mL) at room temperature to which solution ammonium chloride (327 mg) was added. Iron (1.88 g) was then added to the reaction solution which was stirred at 90° C. for 2 hours. The reaction solution was cooled to room temperature and filtered with celite. The resulting filtrate was concentrated, diluted with ethyl acetate, washed with water, washed with a brine and dried over anhydrous magnesium sulphate and the solvent was distilled off. The titled compound (2.63 g) having the following physical properties was thus obtained.

$^1$H-NMR (CDCl$_3$): δ 7.36-7.00, 6.89, 6.60, 6.36, 5.12, 1.62.

Example 3: Benzyl 2-methyl-2-{3-[3-{[(2,2,2-trichloroethoxy)carbonyl]amino}-5-(trifluoromethyl)phenoxy]phenyl}propanoate

[C 16]

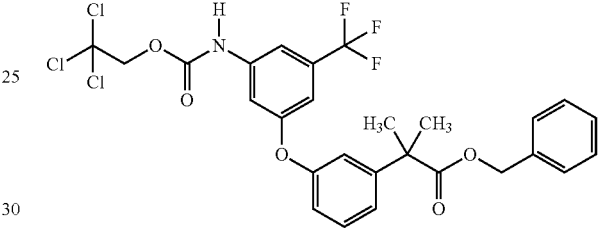

The compound (2.63 g) produced in Example 2 was dissolved in ethyl acetate (50 mL) at room temperature. Sodium hydrogen carbonate (2.57 g) was added to the solution and while stirring, 2,2,2-trichloroethyl chloroformate (0.824 mL) was added dropwise. The reaction solution was stirred for 4 hours, washed twice with water, washed with a brine and dried over anhydrous magnesium sulphate and the solvent was distilled off. The resulting residue was purified by silica gel chromatography (hexane:ethyl acetate=100:0→0:100) to give the titled compound (3.33 g) having the following physical properties.

$^1$H-NMR (CDCl$_3$): δ 7.50-6.90, 5.12, 4.82, 1.61.

Example 4: 3-cyclohexyl-3-pyrrolidinol

[C 17]

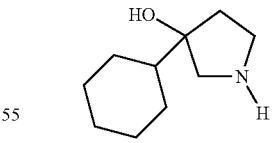

To a frame-dried three-neck flask, lanthanum chloride bis(lithium chloride) (LaCl$_3$.2LiCl) (0.6 M, 100 mL) was added. Bromo(cyclohexyl)magnesium (1 M, 33 mL) was added thereto and under an argon atmosphere, the mixture was stirred at room temperature for 1 hour. At 0° C., a solution of benzyl 3-oxo-1-pyrrolidine carboxylate (5.00 g) in tetrahydrofuran (THF) (10 mL) was added dropwise to the reaction solution which was then heated gradually and stirred overnight at room temperature. To the reaction solution, 10% acetic acid (100 mL) was added and stirred for 15 minutes. The organic layer was then separated and the solvent was distilled off. The resulting residue was partially purified by silica gel chromatography (hexane:ethyl acetate=9:1→0:100) and after distillation of the solvent, diluted with methanol (50 mL) and ethyl acetate (50 mL). To the diluted solution, 5% palladium-carbon (100 mg) was added and under a hydrogen atmosphere, stirred at room temperature for 2 hours. The solution was filtered with celite and the solvent was distilled off to give the titled compound having the following physical properties as 1.40 g of the primary crystal and 2.0 g of the residue.

$^1$H-NMR (CD$_3$OD): δ 3.40-3.20, 2.00-1.20.

Example 5: 2-{3-[3-{[(3-cyclohexyl-3-hydroxy-1-pyrrolidinyl)carbonyl]amino}-5-(trifluoromethyl)phenoxy]phenyl}-2-methylpropanoic acid

[C 18]

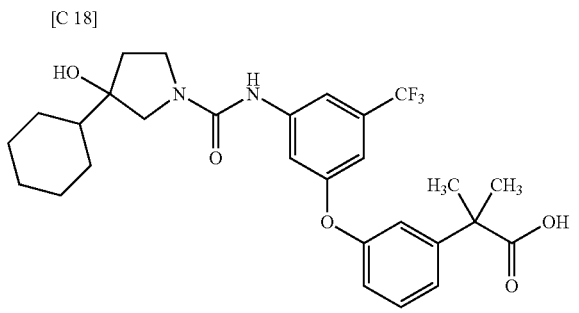

The compound (357 mg) produced in Example 3 and the compound (100 mg) produced in Example 4 were added to DMF (1 mL) and stirred in a microwave reactor (CEM Corporation, DISCOVER) under microwave irradiation at 90° C. for 15 minutes. The reaction solution was cooled to room temperature, diluted with ethyl acetate, washed twice with water, washed with a brine and dried over anhydrous magnesium sulphate and the solvent was distilled off. The resulting residue was partially purified by silica gel chromatography (hexane:ethyl acetate=9:1→0:100) and after distillation of the solvent, diluted with methanol (5 mL) and ethyl acetate (5 mL). To the solution, 5% palladium-carbon (10 mg) was added and stirred under a hydrogen atmosphere at room temperature for 2 hours. The solution was filtered with celite and the solvent was distilled off to give the titled compound (199 mg) having the following physical properties.

TLC: Rf 0.33 (dichloromethane:methanol=10:1);
$^1$H-NMR (CDCl$_3$): δ 7.36-7.23, 7.18-7.15, 7.12-7.10, 6.95-6.89, 6.48, 3.65-3.46, 3.27, 2.00-1.54, 1.45-1.08.

Example 5 (1) to 5 (7)

The following Example compounds were obtained by carrying out the processes with the same purposes as Example 1→Example 2→Example 3→Example 5 using benzyl 2-(3-hydroxyphenyl)-2-methylpropanoate or alternatively a corresponding phenol derivative and the compound produced in Example 4 or alternatively a corresponding piperidine derivative.

Example 5 (1): 4-cyclopentyl-4-hydroxy-N-[3-{4-[(methylsulphonyl)carbamoyl]phenoxy}-5-(trifluoromethyl)phenyl]-1-piperidine carboxamide

[C 19]

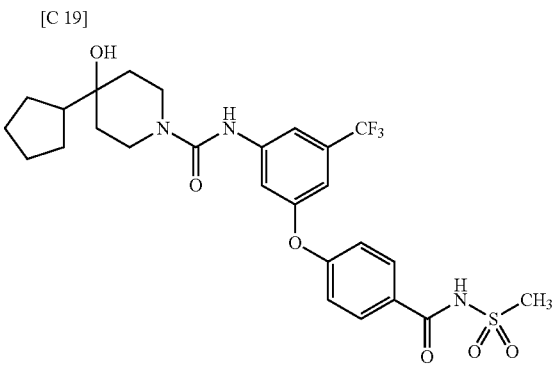

TLC: Rf 0.21 (dichloromethane:methanol=10:1);
$^1$H-NMR (CD$_3$OD): δ 8.02, 7.63-7.53, 7.47-7.36, 7.13-7.02, 6.96-6.87, 4.01-3.78, 3.24, 3.27-3.16, 1.99-1.75, 1.72-1.35.

Example 5 (2): 4-cyclopentyl-N-[3-{4-[(ethylsulphonyl)carbamoyl]phenoxy}-5-(trifluoromethyl)phenyl]-4-hydroxy-1-piperidine carboxamide TLC: Rf 0.26 (dichloromethane:methanol=10:1);
$^1$H-NMR (CD$_3$OD): δ 8.02, 7.62-7.55, 7.46-7.39, 7.15-7.03, 6.95-6.88, 4.00-3.83, 3.41, 3.28-3.16, 1.98-1.78, 1.72-1.40, 1.36.

Example 5 (3): 1-{4-[3-{[(3-cyclohexyl-3-hydroxy-1-pyrrolidinyl)carbonyl]amino}-5-(trifluoromethyl)phenoxy]phenyl}cyclopropanecarboxylic acid TLC: Rf 0.56 (dichloromethane:methanol=10:1);
$^1$H-NMR (CDCl$_3$): δ 7.50, 7.37-7.28, 7.23, 7.00-6.89, 6.42, 3.66-3.54, 3.50, 3.31, 2.02-1.58, 1.32-1.18.

Example 5 (4): 2-{4-[3-{[(3-cyclohexyl-3-hydroxy-1-pyrrolidinyl)carbonyl]amino}-5-(trifluoromethyl)phenoxy]phenoxy}-2-methylpropanoic acid TLC: Rf 0.17 (dichloromethane:methanol=10:1);
$^1$H-NMR (CDCl$_3$): δ 7.32-7.24, 6.96-6.86, 6.49, 3.66-3.44, 3.30, 2.01-1.52, 1.45-1.13.

Example 5 (5): 1-{4-[3-{[(3-cyclohexyl-3-hydroxy-1-pyrrolidinyl)carbonyl]amino}-5-(trifluoromethyl)phenoxy]phenoxy}cyclopropanecarboxylic acid TLC: Rf 0.11 (dichloromethane:methanol=10:1);
$^1$H-NMR (CDCl$_3$): δ 7.63-7.58, 7.50-7.46, 7.12-7.00, 6.93-6.88, 3.73-3.64, 3.57, 3.39, 2.10-1.71, 1.64-1.55, 1.52-1.26, 1.25-1.18.

Example 5 (6): 1-{4-[3-{[(3-cyclohexyl-3-hydroxy-1-pyrrolidinyl)carbonyl]amino}-5-(trifluoromethyl)phenoxy]phenyl}cyclobutanecarboxylic acid TLC: Rf 0.69 (chloroform:methanol=5:1);
$^1$H-NMR (CD$_3$OD): δ 7.65, 7.41, 7.29, 6.97, 6.81, 3.60-3.30, 2.80, 2.40, 2.00-1.08.

Example 5 (7): 1-{4-[3-{[(3-cyclohexyl-3-hydroxy-1-pyrrolidinyl)carbonyl]amino}-5-(trifluoromethyl)phenoxy]phenyl}cyclopentanecarboxylic acid TLC: Rf 0.46 (chloroform:methanol=5:1);
¹H-NMR (CD₃OD): δ 7.65, 7.46, 7.28, 6.95, 6.80, 3.60-3.20, 2.60, 2.00-1.08.

Example 6: (+)-1-{4-[3-{[(3-cyclohexyl-3-hydroxy-1-pyrrolidinyl)carbonyl]amino}-5-(trifluoromethyl)phenoxy]phenyl}cyclobutanecarboxylic acid and (−)-1-{4-[3-{[(3-cyclohexyl-3-hydroxy-1-pyrrolidinyl)carbonyl]amino}-5-(trifluoromethyl)phenoxy]phenyl}cyclobutanecarboxylic acid The compound produced in Example 5 (6) was subjected to optical resolution with HPLC (column used: Daicel Corporation, CHIRALPAK AD (4.6 mm×250 mm); developing solvent: hexane:ethanol:trifluoroacetic acid=50:50:1; flow rate: 1 mL/min). Under the above optical resolution conditions, optically active substances of Example 5 (6) were obtained at the first peak (retention time: about 4.5 min) and at the second peak (retention time: about 5.5 min), respectively. The optical rotation of the compound obtained at the first peak was as follows.

$[\alpha]_D = -25.8$ (CHCl₃, C=0.33).

Therefore, it was found that the compound at the first peak was the dextrorotary optical substance of Example 5 (6) and the compound at the second peak was the levorotatory optical substance of Example 5 (6).

Example 6 (1): (+)-2-{3-[3-{[(3-cyclohexyl-3-hydroxy-1-pyrrolidinyl)carbonyl]amino}-5-(trifluoromethyl)phenoxy]phenyl}-2-methylpropanoic acid and (−)-2-{3-[3-{[(3-cyclohexyl-3-hydroxy-1-pyrrolidinyl)carbonyl]amino}-5-(trifluoromethyl)phenoxy]phenyl}-2-methylpropanoic acid From the compound produced in Example 5, dextrorotary and levorotatory optical substances were obtained under the optical resolution conditions as described in Example 6.

Example 7: 3-{[(4-hydroxy-4-isobutyl-1-piperidinyl)carbonyl]amino}-5-(trifluoromethyl)benzoic acid The titled compound (957 mg) having the following physical properties was obtained by carrying out the process with the same purpose as Example 5 using 4-isobutyl-4-piperidinol and the compound obtained by carrying out the processes with the same purposes as Example 2→Example 3 using methyl 3-nitro-5-(trifluoromethyl)benzoate (5.3 g) instead of the compound produced in Example 1.

TLC: Rf 0.18 (dichloromethane:methanol:acetic acid=100:10:1);
ESI-MS (Pos. 20 V) 389 (M+H).

Example 8: 2-(4-{[3-{[(4-hydroxy-4-isobutyl-1-piperidinyl)carbonyl]amino}-5-(trifluoromethyl)benzoyl]oxy}phenyl)-2-methylpropanoic acid

[C 21]

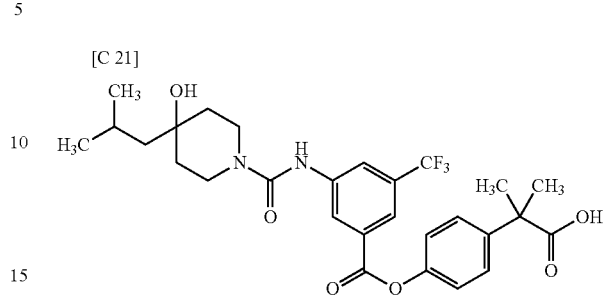

The compound (150 mg) produced in Example 7 was dissolved in DMF (1 mL) and benzyl 2-(4-hydroxyphenyl)-2-methylpropanoate (125 mg), 1-ethyl-3-(3-dimethylaminopropyl)carbodiimide hydrochloride (EDC) (111 mg), 1-hydroxybenzotriazole monohydrate (HOBt) (78.2 mg) and diisopropylethylamine (100 μL) were added thereto and stirred overnight at room temperature. The reaction solution was diluted with ethyl acetate, washed twice with water, washed with a brine and dried over anhydrous magnesium sulphate and the solvent was distilled off. The resulting residue was partially purified by silica gel chromatography (hexane:ethyl acetate=9:1→0:100), the solvent was distilled off and the solution was diluted with methanol (1 mL) and ethyl acetate (1 mL) To the solution, 5% palladium-carbon (10 mg) was added and under a hydrogen atmosphere, stirred at room temperature for 2 hours. The reaction solution was filtered with celite and the solvent was distilled off to give the titled compound (27.5 mg) having the following physical properties.

TLC: Rf 0.68 (chloroform:methanol=5:1);
¹H-NMR (CDCl₃): δ 8.20-6.80, 3.90, 3.14, 1.80, 1.70-1.50, 1.62, 1.43, 0.99.

Example 9: 1-{4-[3-chloro-5-({[4-(4-fluorophenyl)-4-hydroxy-1-piperidinyl]carbonyl}amino)phenoxy]phenoxy}cyclopropanecarboxylic acid The titled compound having the following physical properties was obtained by carrying out the processes with the same purposes as Example 1→Example 2→Example 3→Example 5 using 1,3-dinitro-5-chlorobenzene, a corresponding phenol derivative instead of benzyl 2-(3-hydroxyphenyl)-2-methylpropanoate and a corresponding piperidine derivative instead of the compound produced in Example 4.

TLC: Rf 0.14 (chloroform:methanol=9:1);
¹H-NMR (CD₃OD): δ 7.55, 7.25, 7.10-6.80, 6.55, 4.05, 3.29, 2.99, 1.75, 1.54, 1.20.

Example 10: 2-[4-(3-fluoro-5-{[(4-hydroxy-4-isobutyl-1-piperidinyl)carbonyl]amino}phenoxy)phenyl]-2-methylpropanoic acid The titled compound having the following physical properties was obtained by carrying out the processes with the same purposes as Example 1→Example 2→Example 3→Example 5 using 1,3-dinitro-5-fluorobenzene, benzyl 2-(4-hydroxyphenyl)-2-methylpropanoate and a corresponding piperidine derivative instead of the compound produced in Example 4.

TLC: Rf 0.49 (chloroform:methanol=9:1);
¹H-NMR (CDCl₃): δ 7.30, 7.00, 6.65, 6.58, 6.30, 3.74, 3.25, 1.80-1.50, 1.41, 0.98.

Experimental Examples

The effects of the present compounds were verified based on the experimental methods shown hereinbelow as the biological experimental example and physical experimental example.

Biological Experimental Example 1: Evaluation of S1P$_2$ (EDG-5) Antagonistic Activity by Monitoring the Change in Intracellular Calcium Ion Concentration Chinese hamster ovary (CHO) cells overexpressing the human S1P$_2$ (EDG-5) gene were cultured in a Ham's F12 medium containing 10% fetal bovine serum (FBS), an antibiotic/antifungal agent and G418. CHO cells overexpressing the rat S1P$_2$ (EDG-5) gene were cultured in a Ham's F12 medium containing 10% FBS, penicillin/streptomycin and blasticidin S. The cultured cells were incubated in a Fura2-AM solution (5 μM) [a Ham's F12 medium containing FBS (10%), HEPES buffer (20 mM, pH 7.2 to 7.5) and probenecid (2.5 mM)] at 37° C. for 60 minutes. The cells were washed twice with a Hanks' balanced saline containing HEPES buffer (20 mM, pH 7.2 to 7.5) and probenecid (2.5 mM) and immersed in the same solution. A plate was mounted on a fluorescence-based drug screening system and the intracellular calcium ion concentration was measured for 30 seconds without stimulation. A test substance (the final concentration of human S1P$_2$: 0.25 nM to 25 μM and the final concentration of rat S1P$_2$: 0.25 nM to 2.5 μM) or a dimethyl sulphoxide (DMSO) solution was added and after 3 minutes S1P (final concentration: 30 or 300 nM) was added and the increase in the intracellular calcium ion concentration before and after the addition of S1P was measured with an interval of 3 seconds (excitation wavelength: 340 nm and 380 nm, fluorescence wavelength: 540 nm).

The S1P$_2$ (EDG-5) antagonistic activity was calculated as a suppression (%) from the following formula, wherein A is a control value which was a peak value after addition of S1P (final concentration: 30 or 300 nM) in the wells added with DMSO without a test substance and B is an increased amount after addition of S1P in the cells treated with the test substance:

[M 1]

$$\text{Suppression (\%)} = [(A-B)/A] \times 100$$

The IC$_{50}$ value was calculated as the concentration of the present compound which exhibits the suppression of 50%.

Comparative compounds used were the compounds disclosed in Example 1 (64) (hereinafter referred to as comparative compound A) and Example 1 (85) (hereinafter referred to as comparative compound B) in Patent Document 3 (WO 2004/002531). The structural formulae of the comparative compounds are shown below respectively.

[C22]

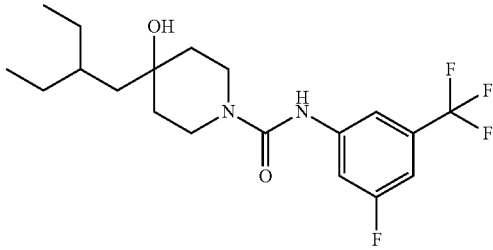

Comparative compound A

[C23]

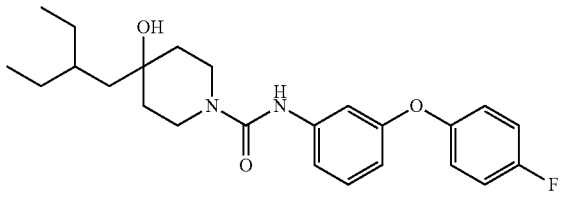

Comparative compound B

The human and rat S1P$_2$ (EDG-5) antagonistic activities of the present compounds and comparative compounds are shown in the following Table 1.

TABLE 1

| | S1P$_2$ antagonistic activity IC$_{50}$ (nM) | |
|---|---|---|
| Compound | Human | Rat |
| Comparative compound A | 1600 | 72 |
| Comparative compound B | 1200 | 27 |
| Example 5 (7) | 8.4 | 5.1 |
| Example 5 (1) | 4.6 | 9.4 |
| Example 8 | 7.3 | 3.0 |

As a result, it was found that the present compounds have significantly improved human S1P$_2$ antagonistic activity compared to the comparative compounds. In addition, the present compounds also have improved difference in the S1P$_2$ antagonistic activity between species, i.e. between human and rat and thus may allow extrapolation of the efficacy obtained in rat pathological models to human.

Physical Experimental Example 2: Solubility Measurement

A solution for obtaining a calibration curve was prepared by diluting a test substance (10 mmol/L, DMSO solution) in acetonitrile and adding acetonitrile containing an internal standard substance (warfarin) to adjust to 0.1, 0.4 and 2 μmol/L. A sample solution was prepared by adding to 495 μL (pH 6.8) of the second solution defined in Japanese Pharmacopoeia (a solution used was obtained by adding water to 250 mL of a 0.2 mol/L potassium dihydrogen phosphate reagent solution and 118 mL of a 0.2 mol/L sodium hydroxide reagent solution to adjust to 1000 mL) 5 μL of a test substance (10 mmol/L, DMSO solution), stirring at room temperature for 5 hours, transferring the obtained solution to a plate with a filter for vacuum filtration, diluting 20 μL of the filtrate with acetonitrile and adding acetonitrile containing the internal standard. The solution for obtaining a calibration curve and the sample solution (5 μL each) were injected to LC-MS/MS (Discovery Max from Thermo Scientific) for quantification (quantification range: 0.1 to 2 μmol/L). The solubility was calculated by multiplying the quantified value by 50. When the quantified value was outside of the quantification range, the solubility was expressed as <5 μmol/L or 100 μmol/L.

The solubility of the present compounds and the comparative compounds is shown in the following Table 2.

TABLE 2

| Compound | Solubility (μmol/L) |
|---|---|
| Comparative compound A | <5 |
| Comparative compound B | <5 |
| Example 5 (7) | 74 |
| Example 5 (1) | 72 |
| Example 8 | 90 |

As a result, it was found that the present compounds have superior solubility compared to the comparative compounds.

Formulation Examples

Formulation Example 1

The following components were mixed and then compressed to make tablets according to the conventional method to obtain 10,000 tablets respectively containing 10 mg of the active ingredient per tablet.

1-{4-[3-{[(3-cyclohexyl-3-hydroxy-1-pyrrolidinyl)carbonyl]amino}-5-(trifluoromethyl)phenoxy]phenyl}cyclopentanecarboxylic acid 100 g Carboxymethylcellulose calcium 20 g Magnesium stearate 10 g Microcrystalline cellulose 870 g Formulation Example 2

The following components were mixed according to the conventional method, then filtered through a dust removal filter, divided at 5 ml per ampoule, sterilized by heating in an autoclave to obtain 10,000 ampoules respectively containing 20 mg of the active ingredient per ampoule.

1-{4-[3-{[(3-cyclohexyl-3-hydroxy-1-pyrrolidinyl)carbonyl]amino}-5-(trifluoromethyl)phenoxy]phenyl}cyclopentanecarboxylic acid 200 g Mannitol 20 g Distilled water 50 L

INDUSTRIAL APPLICABILITY

The present compound has high human $S1P_2$ antagonistic activity and thus is useful for therapy of $S1P_2$-mediated diseases such as diseases resulting from vascular constriction and fibrosis.

The invention claimed is:

1. A compound represented by the general formula (I):

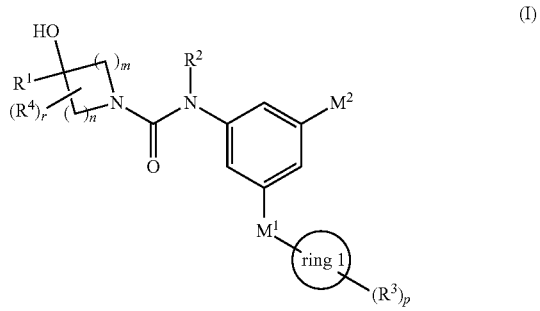

wherein $R^1$ represents (1) a C1-8 alkyl group which can be substituted with 1 to 5 $R^{21}$ groups, (2) a C2-8 alkenyl group which can be substituted with 1 to 5 $R^{21}$ groups, (3) a C2-8 alkynyl group which can be substituted with 1 to 5 $R^{21}$ groups or (4) a C3-7 carbocycle which can be substituted with 1 to 5 substituents selected from the group consisting of a C1-4 alkyl group, a C1-4 haloalkyl group, a C1-4 alkoxy group and a halogen atom;

$R^{21}$ represents (1) a halogen atom, (2) $OR^{22}$ (in the group, $R^{22}$ represents (1) a hydrogen atom, (2) a C1-4 alkyl group or (3) a C1-4 haloalkyl group), (3) —$NR^{23}R^{24}$ (in the group, $R^{23}$ and $R^{24}$ respectively and independently represent (1) a hydrogen atom or (2) a C1-4 alkyl group) or (4) an oxo group;

$R^2$ represents (1) a hydrogen atom, (2) a C1-4 alkyl group or (3) a C1-4 haloalkyl group;

$R^3$ represents (1) a halogen atom, (2) a C1-4 alkyl group, (3) a C1-4 haloalkyl group, (4) a C1-4 alkoxy group, (5) a hydroxy group, (6) -L-$CONR^6R^7$, (7) -L-$SO_2R^8$ or (8) -L-$COOR^9$;

$R^4$ represents (1) a halogen atom, (2) a C1-4 alkyl group or (3) a C1-4 haloalkyl group;

L represents (1) a bond, (2) a group represented by the formula:

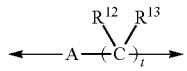

wherein A represents (1) a bond or (2) an oxygen atom; $R^{12}$ and $R^{13}$ respectively and independently represent (1) a hydrogen atom, (2) a C1-4 alkyl group, (3) a hydroxy group or (4) $NH_2$ or (5) $R^{12}$ and $R^{13}$ together with the carbon atom to which they are attached can form a C3-7 carbocycle; and the arrow on the right hand side binds to —$CONR^6R^7$, —$SO_2R^8$ or —$COOR^9$, (3) a C2-4 alkenylene group, (4) a —O—C2-4 alkenylene group, (5) an oxygen atom or (6) a nitrogen atom which can be substituted with a C1-4 alkyl group;

$R^6$ and $R^7$ respectively and independently represent (1) a hydrogen atom, (2) a C1-4 alkyl group, (3) a C1-4 haloalkyl group, (4) a hydroxy group, (5) —$CONR^{15}R^{16}$, (6) —$SO_2NR^{15}R^{16}$, (7) —$COR^{17}$ or (8) —$SO_2R^{17}$, or $R^6$ and $R^7$ together with the nitrogen atom to which they are attached can form a 4- to 7-membered nitrogen-containing saturated heterocycle that can be substituted with a hydroxy group;

$R^8$ represents (1) a C1-4 alkyl group, (2) a C1-4 haloalkyl group or (3) $NR^{10}R^{11}$;

R⁹ represents (1) a hydrogen atom or (2) a C1-8 alkyl group;

R¹⁰ and R¹¹ respectively and independently represent (1) a hydrogen atom, (2) a C1-4 alkyl group, (3) —CONR¹⁵R¹⁶, (4) —SO₂NR¹⁵R¹⁶, (5) —COR¹⁷ or (6) —SO₂R¹⁷;

the ring 1 represents a benzene, cyclohexane or pyridine ring;

R¹⁵ and R¹⁶ respectively and independently represent (1) a hydrogen atom, (2) a C1-4 alkyl group or (3) a 5- to 7-membered cyclic group;

R¹⁷ represents (1) a C1-4 alkyl group or (2) a 5- to 7-membered cyclic group;

M¹ represents (1) a bond, (2) —C(O)—, (3) —O—, (4) —S—, (5) —C(O)O—, (6) —CH₂O— or (7) —C(O)NH—;

M² represents a halogen atom or a C1-4 haloalkyl group;

n represents an integer of 1 to 2;

m represents an integer of 1 to 2;

p represents an integer of 0 to 5;

r represents an integer of 0 to 4;

t represents an integer of 1 to 4;

when p is 2 or more, a plurality of R³ groups can be the same or different;

when r is 2 or more, a plurality of R⁴ groups can be the same or different; and when t is 2 or more, a plurality of R¹² and R¹³ groups can be respectively the same or different;

a salt thereof, a solvate thereof or an N-oxide thereof.

2. The compound according to claim 1, wherein R¹ is (1) a C1-8 alkyl group which can be substituted with 1 to 5 R²¹ groups, or (2) a C3-7 carbocycle which can be substituted with 1 to 5 substituents selected from the group consisting of a C1-4 alkyl group, a C1-4 haloalkyl group, a C1-4 alkoxy group and a halogen atom, a salt thereof, a solvate thereof or an N-oxide thereof.

3. The compound according to claim 1 or 2, wherein M is (1) —O— or (2) —C(O)O—, a salt thereof, a solvate thereof or an N-oxide thereof.

4. The compound according to claim 1, which is represented by the general formula (I-1):

wherein R¹⁻¹ represents (1) a C1-8 alkyl group which can be substituted with 1 to 5 R²¹ groups, or (2) a C3-7 carbocycle which can be substituted with 1 to 5 substituents selected from the group consisting of a C1-4 alkyl group, a C1-4 haloalkyl group, a C1-4 alkoxy group and a halogen atom, a salt thereof, a solvate thereof or an N-oxide thereof.

5. The compound according to claim 4, wherein R² is a hydrogen atom, a salt thereof, a solvate thereof or an N-oxide thereof.

6. The compound according to claim 4, which is 2-{3-[3-{[(3-cyclohexyl-3-hydroxy-1-pyrrolidinyl)carbonyl]amino}-5-(trifluoromethyl)phenoxy]phenyl}-2-methylpropanoic acid, 4-cyclopentyl-4-hydroxy-N-[3-{4-[(methylsulphonyl)carbamoyl]phenoxy}-5-(trifluoromethyl)phenyl]-1-piperidine carboxamide, 4-cyclopentyl-N-[3-{4-[(ethylsulphonyl)carbamoyl]phenoxy}-5-(trifluoromethyl)phenyl]-4-hydroxy-1-piperidine carboxamide, 1-{4-[3-{[(3-cyclohexyl-3-hydroxy-1-pyrrolidinyl)carbonyl]amino}-5-(trifluoromethyl)phenoxy]phenyl}cyclopropanecarboxylic acid, 2-{4-[3-{[(3-cyclohexyl-3-hydroxy-1-pyrrolidinyl)carbonyl]amino}-5-(trifluoromethyl)phenoxy]phenoxy}-2-methylpropanoic acid, 1-{4-[3-{[(3-cyclohexyl-3-hydroxy-1-pyrrolidinyl)carbonyl]amino}-5-(trifluoromethyl)phenoxy]phenoxy}cyclopropanecarboxylic acid, 1-{4-[3-{[(3-cyclohexyl-3-hydroxy-1-pyrrolidinyl)carbonyl]amino}-5-(trifluoromethyl)phenoxy]phenyl}cyclobutanecarboxylic acid, 1-{4-[3-{[(3-cyclohexyl-3-hydroxy-1-pyrrolidinyl)carbonyl]amino}-5-(trifluoromethyl)phenoxy]phenyl}cyclopentanecarboxylic acid, 1-{4-[3-chloro-5-({[4-(4-fluorophenyl)-4-hydroxy-1-piperidinyl]carbonyl}amino)phenoxy]phenoxy}cyclopropanecarboxylic acid or 2-[4-(3-fluoro-5-{[(4-hydroxy-4-isobutyl-1-piperidinyl)carbonyl]amino}phenoxy)phenyl]-2-methylpropanoic acid, a salt thereof, a solvate thereof or an N-oxide thereof.

7. The compound according to claim 4, which is 4-cyclopentyl-4-hydroxy-N-[3-{4-[(methylsulphonyl)carbamoyl]phenoxy}-5-(trifluoromethyl)phenyl]-1-piperidine carboxamide or 1-{4-[3-{[(3-cyclohexyl-3-hydroxy-1-pyrrolidinyl)carbonyl]amino}-5-(trifluoromethyl)phenoxy]phenyl}cyclopentanecarboxylic acid, a salt thereof, a solvate thereof or an N-oxide thereof.

8. A pharmaceutical composition comprising the compound represented by the general formula (I), the salt thereof, the solvate thereof or the N-oxide thereof according to claim 1.

9. A method for treating a S1P2-mediated disease comprising administering an effective amount of the compound represented by the general formula (I), the salt thereof, the solvate thereof or the N-oxide thereof according to claim 1 to a mammal, wherein the S1P2-mediated disease is fibrosis, peripheral arterial occlusive disease, hepatitis, hepatic cirrhosis, hepatic failure, or a disease resulting from vascular constriction wherein the disease is cerebral vasospastic disease, cardiac vasospastic disease, coronary vasospastic disease, hypertension, pulmonary hypertension, myocardial infarction, angina, arrhythmia, portal hypertension, varix, ascites, splenomegaly or hepatic encephalopathy.

10. The method according to claim 9, which comprises persistently reducing portal pressure.

11. The method according to claim 10, wherein the compound can be administered once daily.

12. A method for antagonizing S1P2 receptors in a mammal, comprising administering an effective amount of the compound represented by the general formula (I), the salt thereof, the solvate thereof or the N-oxide thereof according to claim 1 to the mammal.

13. The compound according to claim 1, which is 2-(4-{[3-{[(4-hydroxy-4-isobutyl-1-piperidinyl)carbonyl]amino}-5-(trifluoromethyl)benzoyl[oxy}phenyl)-2-methylpropanoic acid, a salt thereof, a solvate thereof or an N-oxide thereof.

14. The compound according to claim 4, which is (+)-1-{4-[3-{[(3-cyclohexyl-3-hydroxy-1-pyrrolidinyl)carbonyl]amino}-5-(trifluoromethyl)phenoxy]phenyl}cyclobutanecarboxylic acid, (−)-1-{4-[3-{[(3-cyclohexyl-3-hydroxy-1-pyrrolidinyl)carbonyl]amino}-5-(trifluoromethyl)phenoxy]phenyl}cyclobutanecarboxylic acid, (+)-2-{3-[3-{[(3-cyclohexyl-3-hydroxy-1-pyrrolidinyl)carbonyl]amino}-5-(trifluoromethyl)phenoxy]phenyl}-2-methylpropanoic acid, or (−)-2-{3-[3-{[(3-cyclohexyl-3-hydroxy-1-pyrrolidinyl)carbonyl]amino}-5-(trifluoromethyl)phenoxy]phenyl}-2-methylpropanoic acid, a salt thereof, a solvate thereof or an N-oxide thereof.

* * * * *